United States Patent [19]
Urry

[11] Patent Number: 5,900,405
[45] Date of Patent: May 4, 1999

[54] POLYMERS RESPONSIVE TO ELECTRICAL ENERGY

[75] Inventor: Dan W. Urry, Birmingham, Ala.

[73] Assignee: Bioelastics Research, Ltd., Birmingham, Ala.

[21] Appl. No.: 08/487,594

[22] Filed: Jun. 7, 1995

Related U.S. Application Data

[63] Continuation-in-part of application No. 08/187,441, Jan. 24, 1994, abandoned.

[51] Int. Cl.[6] ........................................... F03G 7/00
[52] U.S. Cl. ................................. 514/17; 514/14; 514/15; 514/16
[58] Field of Search ................................ 514/15, 16, 17, 514/14

[56] References Cited

U.S. PATENT DOCUMENTS

| | | | |
|---|---|---|---|
| 4,474,851 | 10/1984 | Urry | 428/373 |
| 5,085,055 | 2/1992 | Urry | 60/527 |

FOREIGN PATENT DOCUMENTS

WO 91/05816   5/1991   WIPO .

OTHER PUBLICATIONS

Irie, "Properties and Applications of Photoresponsive Polymers" Pure & Applied Chem., vol. 62, No. 8, pp. 1495–1502, 1990.

Urry et al., "Hydrophobicity–Induced pK Shifts in Elastin Protein–Based Polymers" Biopolymers, vol. 32, pp. 373–379, 1992.

Urry et al. Caplus An # 1992:651752.

Urry et al. Caplus An # 1993:560799.

*Primary Examiner*—Cecilia J. Tsang
*Assistant Examiner*—Patrick R. Delaney
*Attorney, Agent, or Firm*—Cooley Godward LLP

[57] ABSTRACT

A composition that expands or contracts upon a change in exposure to electrical energy is provided that comprises a protein or protein-based polymeric material having an inverse temperature transition in the range of liquid water, wherein at least a fraction of the monomers in the polymer contain an electrical energy-responsive group that undergoes a change in hydrophobicity or polarity upon a change in exposure to electrical energy and is present in an amount sufficient to provide a shift in the inverse temperature transition of the polymer upon the change in exposure to electrical energy. Compositions of the invention, including those further containing a side-chain chemical couple, can be used in a variety of different applications to produce mechanical work, cause turbidity changes, cause chemical changes in an enclosed environment, or transduce other free energies by varying the exposure to electrical energy on the composition. The degree and efficiency of mechanical or chemical change can be controlled by, inter alia, selection of the type, amount, position, and mole fraction of the electrical energy-responsive side chain group and hydrophobic residues in the polymer.

25 Claims, 3 Drawing Sheets

POLYMERS RESPONSIVE TO ELECTRICAL ENERGY

CONTINUATION STATUS

This application is a continuation-in-part of U.S. Ser. No. 08/187,441, filed Jan. 24, 1994, now abandoned which is herein incorporated by reference.

This work was supported in part by the NSF Materials Research Laboratory at the University of Massachusetts and by Contract Nos. N00014-90-C-0265 and N00014-89-J-1970 from the Department of the Navy, Office of Naval Research. Accordingly the Government of the United States may have certain rights in this invention as a result of governmental support.

INTRODUCTION

1. Technical Field

The present invention is in the field of polymers and is particularly directed to polymers whose physical properties vary as a result of a change of electrochemical potential in the environment of the polymers and to uses thereof that depend on the ability of the polymers to respond to redox changes.

2. Background

Bioelastomeric polypeptides are a relatively new development that arose in the laboratories of one of the present inventors (Dan W. Urry) and which are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746, 4,187,852, 4,589,882, and 4,870,055. U.S. Pat. No. 5,064,430 describes polynonapeptide bioelastomers. Bioelastic polymers are also disclosed in related patents directed to polymers containing peptide repeating units that are prepared for other purposes but which can also contain bioelastic segments in the final polymer: U.S. Pat. Nos. 4,605,413, 4,976,734, and 4,693,718, entitled "Stimulation of Chemotaxis by Chemotactic Peptides"; U.S. Pat. No. 4,898,926, entitled "Bioelastomer Containing Tetra/Pentapeptide Units"; U.S. Pat. No. 4,783,523 entitled "Temperature Correlated Force and Structure Development of Elastin Polytetrapeptide"; U.S. Pat Nos. 5,032,271, 5,085,055 and 5,255,518, entitled "Reversible Mechanochemical Engines Comprised of Bioelastomers Capable of Modulable Temperature Transitions for the Interconversion of Chemical and Mechanical Work"; U.S. Pat. No. 4,500,700, entitled "Elastomeric Composite Material Comprising a Polypeptide"; and U.S. Pat. No. 5,520,516 entitled "Bioelastomeric Materials Suitable for the Protection of Wound Repair Sites." A number of other bioelastic materials and methods for their use are described in pending U.S. patent applications including: U.S. Ser. No. 184,873, filed Apr. 22, 1988, entitled "Elastomeric Polypeptides as Vascular Prosthetic Materials"; and U.S. Ser. No. 07/962,608, filed Oct. 16, 1992, entitled "Bioelastomeric Drug Delivery System." All of these patents and patent applications are herein incorporated by reference, as they describe in detail bioelastomers and/or components thereof and their preparation that can be used in the compositions and methods of the present invention. These bioelastic materials have been proposed for a number of uses and apparatuses, as indicated by the general subject matter of the applications and patents set forth above. The bioelastic compositions and machines, which arose in the laboratories of one of the present inventors, respond to pressure, chemical, and/or thermal changes in the environment by phase transitions (e.g. viscosity or turbidity changes) or by contraction or relaxation to reversibly transduce these energies into mechanical work. For example, polymers and machines capable of baromechanical (pressure-to-mechanical), barochemical, and barothermal transductions have uses that include sensors, actuators and desalinators (See U.S. Pat. No. 5,226,292, which is incorporated herein by reference).

There are a number of publications that describe polymers having the ability to respond to electrochemical stimulation in some predetermined fashion. For example, Urry, *Angew. Chem. Int Ed. Engl.* (1993) 32:819–941, is a review article by one of the present inventors describing how motion and other physical changes of bioelastomers can result from a variety of reversible (and irreversible) chemical changes (including redox reactions) in the structure of the bioelastomeric polymers. U.S. patent application Ser. No. 08/187,441 now abandoned, the parent of the present application, describes these redox changes (as part of its disclosure, which is principally directed to photochemical changes).

Accordingly, a need still exists for elastomeric polymers in which phase transitions, mechanical activity, or free energy transductions are induced and modulated in a relatively clean, remote, and precise fashion, at a macro or micro level, and in which properties including bio-compatibility, hysteresis, half-life, elastic modulus, defined polymer size, efficiency of energy conversion, biological function (e.g. chemotaxis), and polymer structure can be readily achieved and finely adjusted. The present invention provides these and other advantages by providing protein and protein-based bioelastic polymers that are responsive to environmental changes in electrochemical potential to transduce electrical energy into useful work, and by providing machines containing these polymers.

LITERATURE

Reference is made in the following specification to the following publications by giving the publication number in parentheses at the location where cited.

1. Urry, D. W., (1988) *J. Protein Chem.* 7:1–34.
2. Urry, D. W., (1989) *J. Protein Chem.* 7:81–114.
3. Urry, D. W., (1990) *American Chemical Society, Div. of Polymeric Materials: Sci. and Engineering* 62.
4. Hollinger, J. O., Schmitz, J. P., Yaskovich, R., Long, M. M., Prasad, K. U., and Urry, D. W., (1988) *Calacif. Tissue Int.* 42:231–236.
5. Urry, D. W., (1988) *Intl. J. Quantum Chem.: Quantum Biol. Symp.* 15:35–245.
6. Edsall, J. T. and McKenzie, H. A., (1983) *Adv. Biophys.* 16:3–183.
7. Kauzman, W., (1959) *Adv. Protein Chem.* 14:-63.
8. Urry, D. W., Luan, C. H., Harris, R. Dean, and Prasad, Karl U., (1990) *Polymer Preprint Am. Chem. Soc. Div. Polym. Chem.* 31:188–189.
9. Urry, D. W., (1984) *J. Protein Chem.* 3:403–436.
10. Chang, D. K., Venkatachalam, C. M., Prasad, K. U., and Urry, D. W., (1989) *J. of Biomolecular Structure & Dynamics* 6:851–858.
11. Chang, D. K. and Urry, D. W., (1989) *J. of Computational Chemistry* 10:850–855.
12. Urry, D. W., Haynes, B., Zhang, H., Harris, R. D., and Prasad, K. U., (1988) *Proc. Natl. Acad. Sci. USA* 85:3407–3411.
13. Urry, D. W., Peng, Shao Qing, Hayes, Larry, Jaggard, John, and Harris, R. Dean, (1990) *Biopolymers* 30:215–218.

14. Sidman, K. R., Steber, W. D., and Burg, A. W., (1976) In *Proceedings, Drug Delivery Systems* (H. L. Gabelnick, Ed.), DHEW Publication No. (NIH) 77:1238, 121–140.
15. Urry, D. W., Chang, D. K., Zhang, H., and Prasad, K. U., (1988) *Biochem. Biophys. Res. Commun.* 153:832–839.
16. Robinson, A. B., (1974) *Proc. Nat. Acad. Sci. USA* 71:885–888.
17. Urry, D. W. (1982) In *Methods in Enzymology*, (L. W. Cunningham and D. W. Frederiksen, Eds.) Academic Press, Inc. 82:673–716.
18. Urry, D. W., Jaggard, John, Harris, R. D., Chang, D. K., and Prasad, K. U., (1990) In *Progress in Biomedical Polymers (Charles G. Gebelein and Richard L. Dunn, Eds.)*, Plenum Publishing Co., N.Y. pp. 171–178.
19. Urry, D. W., Jaggard, J., Prasad, K. U., Parker, T., and Harris, R. D., (1991) in *Biotechnology and Polymers*, (C. G. Gebelins, ed.), Plenum Press., N.Y. pp. 265–274.
20. Urry, D. W., Harris, R. D., and Prasad, K. U. (1988) *J. Am. Chem. Soc.* 110:3303–3305.
21. Sciortino, F., Palma, M. U., Urry, D. W., and Prasad, K. U., (1988) *Biochem. Biophys. Res. Commun.* 157:1061–1066.
22. Sciortino, F., Urry, D. W., Palma, M. U., and Prasad, K. U., (1990) *Biopolymers* 29:1401–1407.
23. Pitt, C. G. and Schindler, A., (1980) In *Progress in Contraceptive Delivery Systems* (E. Hafez and W. Van Os, Eds.), MTP Press Limited 1:17–46.
24. Urry, D. W. (1990) *Mat. Res. Soc. Symp.* 174:243–250, and references therein.
25. Urry, D. W. (1990) *Expanding Frontiers in Polypeptide and Protein Structural Research in Proteins: Structure, Dynamics and Design*, (V. Renugopalakrishnan, P. R. Carey, S. G. Huang, A. Storer, and I. C. P. Smith, Eds.) Escom Science Publishers B.V., Leiden, The Netherlands (1991) pp. 352–360.
26. Bungenberg de Jong, H. G. and Kruyt, H. R. (1929) *Proc. Kon. Ned. Akad. Wet.* 32:849.
27. Bungenberg de Jong, H. G. and Kruyt, H. R. (1930) *Kolloid-Z* 50:39.
28. Bungenberg de Jong, H. G., (1949) in *Colloid Sci.* (H. R. Kruyt, Ed.) Elsevier, Amsterdam, Vol. 2, Chap. VIII, p. 232.
29. Luan, C. H. and Urry, D. W. (1991) "Solvent Deuteration Enhancement of Hydrophobicity: DSC Study of the Inverse Temperature Transition of Elastin-based Polypeptides" *J. Phys. Chem.* 95:7896–7900.
30. Luan, C. H., Jaggard, J. J., Harris, R. D., and Urry, D. W. (1989) *Intl. J. of Quantum Chem.: Quantum Biol. Symp.* 16:235–244.
31. Urry, D. W., Luan, C. H., Parker, T. M., Gowda, D. C., Prasad, K. U., Reid, M. C., and Safavy, A. (1991) *J. Am. Chem. Soc.* 113:4346–4348.
32. Urry, D. W., Trapane, T. L., and Prasad, K. U. (1985) *Biopolymers* 24:2345–2356.
33. Urry, D. W. (1993) *Angew. Chem. Int. Ed. Engl.* 32:819–841.
34. Urry et al. (1993) *J. Am. Chem. Soc.* 115:7509–7510.
35. Urry, D. W., Hayes, L. C., Gowda, D. C., Parker, T. M. (1991) *Chem. Phys. Lett.* 182, 101–106.
36. Urry, D. W., Hayes, L. C., Gowda, D. C., Harris, C. M., Harris, R. D. (1992) *Biochem. Biophys. Res. Comm.* 188, 611–617.
37. Pattanaik, A., Gowda, D. C., Urry, D. W. (1991) *Biochem. Biophys. Res. Commun.* 178, 539–545.
38. Irie, M. (1990) *Pure and Appl. Chem.* 62, 1495–1502.
39. Urry, D. W., Peng, S. Q., Parker, T. M. (1992) *Biopolymers* 32, 373–379.
40. Fissi, A., Pieroni, O. (1989) *Macromolecules* 22, 115–1120.
41. Ferritto, M. S., Tirrell, D. A. (1990) *Biomaterials* 11, 645–651.
42. Brown, C. (1966) *Acta Crystallogr.* 21, 146–152.
43. Urry, D. W., Luan, C. H., Parker, T. M., Gowda, D. C., Prasad, K. U., Reid, M. C., Safavy, A., (1991) *J. Am. Chem. Soc.* 113, 4356–4348.
44. Urry, D. W., Gowda, D. C., Parker, T. M., Luan, C. H., Reid, M. C., Harris, C. M.; Pattanaik, A.; Harris, R. D. (1992) *Biopolymers* 32:1243–1250.
45. Schild, H. G. (1992) *Prog. Polym. Sci.* 17:163–249.
46. Urry et al. (1981) *J. Am. Chem. Soc.* 103:2080–2089.
47. Urry et al. (1993) *Chem. Phys. Lett.* 201:336–340.
48. Katchalsky, et al. (1960) in Size and Shape of Contractile Polymers: Conversion of Chemical and Mechanical Energy (ed. Wasserman) Pergamon, New York, pp 1–40.
49. Katchalsky et al. (1951) *J. Polym. Sci.* 7:383–412.
50. Kuhn et al. (1950) *Nature* 165:514–516.
51. Urry (1992) *Prog. Biophys. Mol. Biol.* 57:23–57.
52. Urry et al. (1992) *J. Am. Chem. Soc.* 114:8716–8717.

SUMMARY OF THE INVENTION

The present invention is directed to new bioelastomers and to a new use of bioelastic materials, namely as part of a system in which mechanical, chemical, electromagnetic radiation, or pressure-related work occurs (or any or all occur) as a result of a response by the bioelastic material to a change in electrochemical potential (or vice versa; i.e., the process can be reversible). The response is typically a chemical change (bond formation or breaking), and this change results in a change of the mechanical properties (and other properties) of the polymer. The invention provides protein and protein-based bioelastomers that can undergo a phase transition, such as a phase separation, free energy transduction, or contraction or relaxation in response to a change in exposure to electrical energy in its various forms. In addition to the general description of polymers having these properties and their uses, a number of specific improvements over earlier polymers are also provided.

It is a further object of the invention to describe the design parameters by which the conditions under which phase transition, free energy transduction, or contraction and expansion of a composition of the invention can be finely controlled and adjusted. Such design parameters have previously described for other types of energy interaction with polymers and are applied here to redox polymers.

These and other objects of the present invention as will hereinafter become more readily apparent have been accomplished by providing a composition capable of undergoing a phase transition, an absorbance change, or contraction or relaxation in response to a change in electrical energy, which composition includes a protein or protein-based bioelastic polymer containing elastomeric units selected from the group consisting of bioelastic peptide units, wherein at least a fraction of the bioelastic units contain at least one amino acid residue having a side chain substitution reactive to electrical energy to effect a change in the polarity or hydrophobicity of the side chain in an amount sufficient to provide modulation of the inverse temperature transition of the bioelastic polymer. Preferred bioelastic peptide units are bioelastic tetrapeptides, pentapeptides, and nonapeptides as described in the various publication recited herein from the laboratories of the present inventors.

Another object of the invention is to provide compositions capable of $T_t$-type second order energy transductions involving electrical energy. Such compositions include an electroresponsive protein or protein-based bioelastomer wherein a bioelastic unit further includes a second amino acid residue having a side chain or substituted side chain capable of undergoing a change in an aqueous environment (e.g. chemical, photochemical, or conformational change) in response to the electrically induced response of the first responsive side chain. The bioelastic unit with the second amino acid can be the same unit that contains the responsive side chain or can be a separate unit (e.g. in a copolymer).

The transition characteristics of the bioelastomers can be controlled by changes including (a) appropriately varying the chemical composition of the reactive side chain(s) or second side chain(s) couple to effect a change in the hydrophobicity and/or polarity of the responsive side chain upon exposure to electrical energy or in the second side chain couple, (b) varying the mole fraction of the responsive side chain substituent units in the overall polymer, (c) varying the mole fraction of the second side chain couple, (d) varying the composition of the other amino acid residues, (e) varying the location, orientation and attachment of the responsive side chain(s) in relation to the second side chain couple, (f) varying the overall hydrophobicity of the bioelastic unit, and (g) varying the number, location, orientation and attachment of other hydrophobic side chain(s) in relation to the second side chain couple.

The bioelastic polymers as described herein can be used in methods and apparatuses in which mechanical, chemical, pressure-related, thermal or electromagnetic changes occur as a result of changes in the polymer upon a change in exposure to electrical energy. The response (and subsequent polymer activity) can be made either reversible or irreversible by choice of electroresponsive substituents and second couple substituent.

It is a further object of the invention to provide protein and protein-based first-order molecular machines of the $T_t$-type capable of electromechanical transduction in response to a change in exposure to electrical energy to produce useful work.

It is a further object of the invention to provide protein and protein-based second-order molecular machines of the $T_t$-type capable of electrochemical, electrothermal, electromagnetic, or electrobaric energy transductions in response to a change in exposure to electrical energy to produce useful chemical, thermal, electrical or pressure-related work.

The responsiveness of the protein and protein-based bioelastic polymers of the invention, and apparatuses comprising them, to electric energy allows relatively clean, remote and precise induction and modulation of polymer properties, at both the micro and macro level. By remote is meant that the polymer can be modulated without direct physical contact with it or its aqueous environment. The folding and unfolding of the bioelastic polymers of the invention do not display hysteresis, and accordingly the energy transductions and work produced by the bioelastic polymers is repeatedly and reproducibly attained. In addition, the chemical and physical structure of the bioelastic polymers of the invention can be readily adjusted to "poise" the bioelastic polymer to enhance or reduce the extent of folding or unfolding (and thus work produced) in response to electrical energy. In polymers of the invention capable of undergoing $T_t$-type second order electrochemical transductions, poising provides more efficient conversion of electrical energy into chemical energy than were previously available. Protein and protein-based bioelastic polymers as taught herein can be designed to have numerous advantages including biological stability, biological function, and defined polymer size. These advantages are achieved in the present invention by providing polymers composed of easily obtained and coupled monomer units, i.e. amino acids, that are themselves diverse in structure and in chemical properties, and whose side chain groups can be readily modified to contain groups selected from the vast array of well-studied molecules responsive to electrical energy. Furthermore, recombinant peptide-engineering techniques can be advantageously used to produce specific bioelastic peptide backbones, either the bioelastic units or non-elastic biofunctional segments, which can be chemically modified to contain electroresponsive groups.

DESCRIPTION OF THE DRAWINGS

The present invention will be better understood by reference to the following detailed description of the invention and the drawings which form part of the present specification, wherein.

DESCRIPTION OF SPECIFIC EMBODIMENTS

Figure 1:
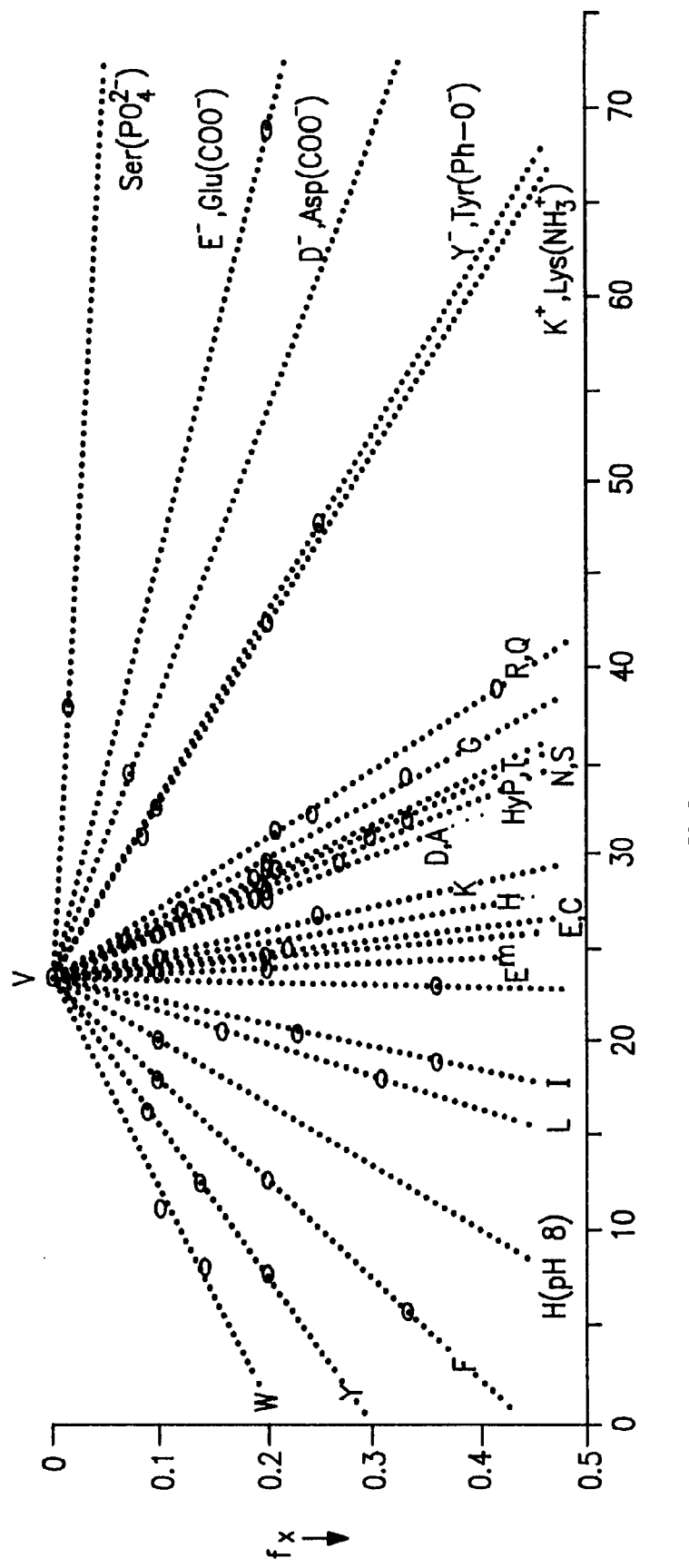
FIG. 1 is a graph showing the relationship of mole fraction of hydrophobic or polar units and the relative hydrophobicity or polarity of those units on the temperature of the inverse temperature transition.

The electrically induced effects of the present invention occur in protein and protein-based bioelastic polymers that display an inverse temperature transition. Preferably the transition occurs in the range of liquid water. Protein and protein-based bioelastic polymers that exhibit an inverse temperature transition, which is a phase transition to a condensed state of greater order in water as temperature increases, are typically polymers that contain both polar and hydrophobic regions. These bioelastic polymers are described in detail herein, but are also described (without the reactive group) in the various patents and other documents listed above that arose in the laboratories of the present inventors.

Examples of a redox couple group capable of a change in the oxidation/reduction state include a dinucleotide e.g. of nicotinamide (NAD) or a flavin (FAD), a quinone, a thio group, or a protoporphrin or the like. For example a quinone is attached to the bioelastomeric polymer or a change in the oxidation/reduction state of a thio group in an amino acid such as Cys. The change in the oxidation state of a quinone attached to an amino acid by the reaction with a linking functional group or in a functional group in the amino acid chain itself is also effective. In one embodiment of the invention, an amino acid is modified by attaching a riboflavin to the carboxylic group of a Glu or Asp residue through formation of an ester linkage or by an amide linkage through an $NH_2$ group of Lys (K) using e.g. N-methyl nicotinate or the like. Protoporphyrins such as protoporphyrin IX can be attached to the amino group of Lys through one of its own carboxylic groups. Heme A can be attached in a similar manner. Change in the oxidation state of, or coordination of a ligand with, the iron atom in a heme attached to an amino acid side chain can also be used as a site of reaction. When a pressure sensitive aromatic functional group is oxidized or reduced, the bioelastomeric polymer exhibits barelectrical transduction or piezoelectric effects. For example, it has been found that attachment of a flavin adenine dinucleotide (FAD) of nicotinamide adenine dinucleotide (NAD) by an amide linkage to a Glu carboxyl group in the bioelastomeric polymer chain results in a protein-based polymer that changes its transition temperature on reduction.

Responsive side chains and their substituents are chosen to result either in an increase in the temperature at which the bioelastomer folds ($T_t$) or a decrease in $T_t$. Thus, in response to a change in exposure to electrical energy, a bioelastomer can either expand or contract, or undergo a phase transition, resulting, for example, in a turbid or a non-turbid solution. A bioelastic polymer of the invention can contain more than one type of electroresponsive side chain, which can differ, for example, by the electrical potential necessary to cause each electrochemical response.

By responsive to electrical energy is meant that a chemical reaction, e.g. ionization, oxidation, reduction, protonation, cleavage, phosphorylation, etc., configurational, e.g. cis-to-trans isomerization, or other chemical change occurs to the side chain group upon a change in exposure to electrical energy, e.g. change in charge density, electrical potential, or presence or absence of electrons available for reaction.

In addition, since the $T_t$ of a protein or protein-based bioelastomer of the invention can be modulated by a change in exposure to electrical energy (in essence the electrical energy results in a variation in the polymer composition without synthesis of a new polymer), the response, e.g. contraction/expansion, phase transition, of the bioelastomer to extrinsic or intrinsic changes, e.g. pressure, pH, salt, concentration, organic solutes, is in turn modulable. This property can now be put to use to achieve mechanical, chemical, thermal or pressure-related work, as described herein.

The electroresponsive protein and protein-based bioelastic polymers of the invention have the unexpected property of "poising," e.g. the same amount of change in hydrophobicity induced by the electrical energy reaction causes a relatively larger effect in polymer response, if the hydrophobicity change is selected (i.e. poised) to occur at a pre-selected value relative to other values where little change occurs. Transduction of electrical energy is more efficient in poised polymers. Poising the electroresponsiveness of the bioelastomer can be achieved by increasing the overall hydrophobicity of the bioelastic unit when the electroresponse results in an increase in hydrophobicity of the electroresponsive side chain. Poising is also achieved by positioning a greater number of hydrophobic groups in closer proximity to the electroresponsive unit undergoing a hydrophobicity change or to the second side chain couple present in polymers for $T_t$-type second order electrotransductions. Alternatively, poising is achieved by increasing or positioning polar groups in the elastomeric unit when the electroresponsive group undergoes an increase in polarity.

Although the invention can be carried out with a number of different protein or protein-based polymers, this specification exemplifies the invention by concentrating on the class of polymers originally identified by the inventor and subsequently modified as taught herein to provide new electroresponsive compounds, compositions, and apparatuses of the invention.

Bioelastic polypeptides have been previously characterized and described in a number of patents and patent applications described above. These materials contain either tetrapeptide, pentapeptide, or nonapeptide monomers which individually act as elastomeric units within the total polypeptide containing the monomeric units. The elasticity of the monomeric units is believed to be due to a series of β-turns in the protein's secondary structure, i.e., the conformation of its peptide chain, separated by dynamic (as opposed to rigid) bridging segments suspended between the β-turns. A β-turn is characterized by a 10-atom hydrogen-bonded ring of the following formula:

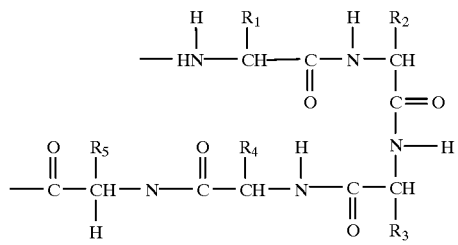

In this formula $R_1$–$R_5$ represent the side groups of the respective amino acid residues. The 10-atom ring consists of the carbonyl oxygen of the first amino acid, the amino hydrogen of the fourth amino acid, and the intervening backbone atoms of amino acids two and three. In this monomeric unit as shown, the remaining backbone atoms of the chain (the remainder of amino acid four, amino acid five, and the first part of amino acid one of the next pentameric unit) form the bridging segment that is suspended between adjacent β-turns. Similar structures are present in elastomeric peptide units of other lengths. Other peptide structures, such as β-barrels, can also impart elasticity to bioelastic polymers. Bioelasticity is imparted by structures that impart internal dampening of chain dynamics upon polymer extension, i.e. oscillation or freedom to rotate about torsional angles or bonds is dampened. The dampening results in reducing the degrees of freedom available in the extended state.

This β-turn-containing structure is described in the prior patents and patent applications cited above and need not be described again in detail. Considerable variations in the amino acids that are present at various locations in the repeating units is possible as long as the multiple β-turns with intervening suspended bridging segments are retained in order to preserve elasticity. Furthermore, it is possible to prepare polypeptides in which these monomeric units are interspersed throughout a larger polypeptide that contains peptide segments designed for other purposes. For example, rigid segments can be included to increase the modulus of elasticity or segments having biological activity (such as chemotaxis or cell attachment) can be included for their biological activity. There appears to be no upper limit to the molecular weight of useful polymers of the invention except that imposed by the processes of making these polymers. Polymers containing up to about 250 pentamers have been synthesized from E. coli using recombinant DNA methods.

These bioelastomeric materials, which include the prototypic poly(Val$^1$-Pro$^2$-Gly$^3$-Val$^4$-Gly$^5$) (referred to herein as "poly(VPGVG)") and poly(Val$^1$-Pro$^2$-Gly$^3$-Gly$^4$) molecules as well as numerous analogues, when combined with water form viscoelastic phases which when cross-linked result in soft, compliant, elastomeric matrices (1–3). The VPGVG-based polypentapeptide (and other bioelastomers) has been shown to be biocompatible both before and after crosslinking (4). As implants, such bioelastic polymers are biodegradable, leading to the release of products natural to the body, such as short peptide chains and free amino acids. These polymers, also referred to as elastomeric polypeptide biomaterials or simply bioelastic materials, can be prepared with widely different water compositions, with a wide range of hydrophobicities, with almost any desired shape and porosity, and with a variable degree of cross-linking by selecting different amino acids for the different positions of the monomeric units and by varying the cross-linking process, e.g. chemical, enzymatic, irradiative, used to form the final product. U.S. Pat. No. 4,589,882, incorporated herein by reference, teaches enzymatic cross-linking by synthesizing block polymers having enzymatically cross-linkable units.

Poly(VPGVG), exhibits an inverse temperature transition (24, 25) in which the polypentapeptide folds and assembles into more ordered structures on raising the temperature with formation of a more dense phase, called the coacervate phase (26–28). A working model for the folded molecular structure called a dynamic β-spiral and the supercoiling assembly of several β-spirals to form a twisted filament has been developed based on a wide range of physical and computational methods (24). On γ-irradiation cross-linking an insoluble elastic matrix is formed wherein, on raising the temperature, the molecular folding and assembly is seen as a macroscopic shrinking and extrusion of water from the matrix. As this thermally driven contraction can be used reversibly to lift weights, the matrix expresses its thermally driven folding as a reversible thermomechanical transduction (24). The temperature at which the folding and assembly occur can be shifted and thus folding and assembly can occur without a change in temperature. This is referred to as the $\Delta T_t$ mechanism (32).

The temperature at which folding and assembly occur can be changed by changing a number of intrinsic or extrinsic changes. The chemical changes that can change the value of $T_t$ may be grouped as intrinsic and extrinsic. Intrinsic to a class of model proteins of 50,000 Da molecular weight or greater are: (a) the concentration of polymer itself, (b) changes in the amino acid composition within the polymeric bioelastic unit, (c) changes in the degree of ionization of functional side chains controlled by changes in pH, (d) the phosphorylation of side chains such as serine by enzymes called kinases, (e) the oxidation or reduction electrically, chemically or enzymatically of a side chain attached to the polymer, and (f) chemical reactions of side chains in response to electromagnetic radiation.

With awareness of the concentration effect and of certain conformational restrictions, the effect of changing the amino acid composition on the value of $T_t$ can be determined. See FIG. 1. The result is a hydrophobicity scale based for the first time directly on the hydrophobic folding and assembly process of interest. This can be demonstrated using the polypentapeptide poly[$f$v(VPGVG)$_2 f_x$(VPGXG)], as an example, where $f$v and $f$x are mole fractions with $f$x+$f$v=1 and where X is any of the naturally occurring amino acid residues or chemical modifications thereof, and $T_t$ is defined as the temperature for half-maximal turbidity. As seen by plotting $f$x versus $T_t$ in FIG. 1 for all of the naturally occurring amino acid residues, more hydrophobic residues than Val, such as Ile(I), Phe(F), etc., lower the temperature of the transition whereas less hydrophobic residues like Ala(A), Gly(G) and polar residues like Asp(COO—)(D$^-$), Lys(NH$_3^+$)(K$^+$), etc. raise the temperature of the transition (i.e., raise the value of $T_t$). The plots are essentially linear. Therefore, on extrapolating the linear plots to $f$x=1, values of $T_t$ are obtained that give an index of relative hydrophobicity (34 and 44, which are both incorporated herein by reference). These values are given in Table 1.

The $T_t$-based hydrophobicity scale depicted in Table 1 is useful for protein engineering of bioelastic polymers of the invention. When a functional side chain or sequence is introduced, for example, to achieve a given free energy transduction, then residue X may be varied to place the value of $T_t$ as desired for the intended protein function. When a given hydrophobic side chain in the repeating pentamer of a protein polymer is replaced by one having an additional hydrophobic CH$_2$ moiety, the value of $T_t$, the temperature of the inverse temperature transition, is lowered in direct proportion to the number of added CH$_2$ moieties. When a given hydrophobic side chain in the protein polymer is replaced by one having fewer CH$_2$ moieties, as when Val is replaced by Ala, the value of $T_t$ is raised in direct proportion to the number of CH$_2$ moieties removed. Thus the value of $T_t$ is clearly related to the hydrophobicity with lower values of $T_t$ indicating greater hydrophobicity and higher values of $T_t$ indicative of more polar or less hydrophobic residues.

TABLE 1

Temperature of the inverse temperature transition, $T_t$ for poly[$f$v(VPGVP),$f$x(VPGXG)].
$T_t$ values are linearly extrapolated to $f$x = 1.

| Amino acid residue X | $T_t$ [° C.] | Correlation coefficient |
|---|---|---|
| Lys (NMeN, red.) [a] | −130 | 1.000 |
| Trp (W) | −90 | 0.993 |
| Tyr (Y) | −55 | 0.999 |
| Phe (F) | −30 | 0.999 |
| His (pH 8) (H) | −10 | 1.000 |
| Pro (P) | (−8) | [b] |
| Leu (L) | 5 | 0.999 |
| Ile (I) | 10 | 0.999 |
| Met (M) | 20 | 0.996 |
| Val (V) | 24 | [c] |
| Glu(COOCH$_3$)(E$^m$) | 25 | 1.000 |
| Glu(COOH)(E) | 30 | 1.000 |
| Cys (C) | 30 | 1.000 |
| His (pH 4) (H$^+$) | 30 | 1.000 |
| Lys(NH$_2$)(K) | 35 | 0.936 |
| Asp(COOH)(D) | 45 | 0.994 |
| Ala (A) | 45 | 0.997 |
| HyP | 50 | 0.998 |
| Asn (N) | 50 | 0.997 |
| Ser (S) | 50 | 0.997 |
| Thr (T) | 50 | 0.999 |
| Gly (G) | 55 | 0.999 |
| Arg (R) | 60 | 1.000 |
| Gln (Q) | 60 | 0.999 |
| Lys(NH$_3^+$)(K$^+$) | 120 | 0.999 |
| Tyr(θ-O$^-$)(Y$^-$) | 120 | 0.996 |
| Lys(NMeN, ox.) [a] | 120 | 1.000 |
| Asp(COO$^-$)(D$^-$) | 170 | 0.999 |
| Glu(COO$^-$)(E$^-$) | 250 | 1.000 |
| Ser(PO$_4^-$) | 1000 | 1.000 |

[a] NMeN represents N-methylnicotinamide pendant on a lysyl side chain, i.e., N-methylnicotinate attached by amide linkage to the ε-NH$_2$ of lysine. The reduced state is N-methyl-1,6-dihydronicotinamide residue.
[b] Calculated.
[c] Serves as reference substance.

Extrinsic chemical changes affecting $T_t$ include the effects of salts, organic solutes and pressure. U.S. Pat. No. 5,226,292 from the laboratory of the present inventors details pressure-related effects. In addition there is a chain length dependence that becomes significant at lower molecular weights where shorter chain lengths result in higher values of $T_t$.

The chemical equivalent, of raising the temperature to achieve ordering in these molecular systems that exhibit inverse temperature transitions, is chemically lowering the transition temperature, $T_t$, at which the folding occurs. By making the polymer more hydrophobic, e.g., Val$^1$→Ile$^1$, the transition temperature is lowered; or by making it more hydrophilic, e.g., Val$^4$→Ala$^4$ or even Val$^4$→Glu$^4$COOH→Glu$^4$COO$^-$, the transition temperature (T$_t$) for coacervate phase formation, is raised. For poly[4 (VPGVG), 1(VPGEG)] where E=Glu, which is equivalent to poly[0.8(VPGVG), 0.2(VPGEG)], it becomes possible in phosphate buffered saline to shift the transition temperature for folding and phase separation from about 20° C. for COOH to about 70° C. for COO$^-$, and at the isothermal condition of 37° C. the cross-linked matrix reversibly relaxes on raising the pH to about 7 and contracts on lowering the pH to about 3 (46). In doing so, weights can be lifted; this is chemomechanical transduction. Specifically, $(\delta\mu/\delta f)_{n=x}<0$ where $\mu$ is chemical potential, $f$ is force and n=x indicates constant composition, i.e., in this case a constant degree of ionization (44). The efficiency of this mechanism of chemomechanical transduction appears to be an order of magnitude greater than that mechanism driven by charge-charge repulsion where $(\delta\mu/\delta f)_n>0$, for example in polymethacrylic acid gels (36). If one recognizes that each chemically induced conformational change to achieve function involves chemomechanical transduction, then it is to be anticipated that proteins utilize this mechanism whenever it is available to achieve chemically induced function. In polymers such as poly(N-isopropylacrylamide) (45) inverse temperature transitions referred to as lower critical solution temperatures (LCST) were observed that were dependent on the content of hydrophobic iso-propyl groups in the polymer. A $\Delta T_t$ type of mechanism was not recognized perhaps because of more-limited control of composition in such polymers prevented the testing for such a model.

The preceding may be called polymer-based chemomechanical transduction. It is also possible to change the temperature of the inverse temperature, T$_t$, chemically by changing the extrinsic variable, the solvent composition, and this may be called solvent-based mechanochemical coupling or chemomechanical transduction. Indeed, a small increase in salt (NaCl) concentration can lower the value of T$_t$ and this change can be used to drive chemomechanical transduction (20). Also, deuterium oxide lowers T$_t$; ethylene glycol lowers T$_t$ (47); and urea raises T$_t$. All of these and many other solutes that change the value of T$_t$ can be used to drive chemomechanical transduction.

Phenomenologically, chemomechanical transduction, as exemplified by poly(VPGVG) and its analogs, results from chemical modulation of the temperature of inverse temperature transitions. More descriptively, it is viewed as chemical modulation of the expression of hydrophobicity with both polymer-based and solvent-based means of altering hydrophobic expression. For polymer-based mechanochemical coupling, the driving force appears to arise from structurally-constrained and sufficiently proximal hydrophobic and polar moieties each competing for their uniquely required hydration structures. In other words, there occurs an apolar-polar interaction free energy of hydration which is generally repulsive due, for example, to a polar species achieving improved structuring of hydration shells by destructuring the clathrate-like (caged) water of hydrophobic moieties or conversely, when the cluster of hydrophobic residues becomes more dominant in achieving its cages of water, by limiting the hydration required by the more polar species. This allows that increasing hydrophobicity can cause an increase in carboxyl pK$_a$ by raising the free energy of the more polar species due to inadequate hydration (25). For solvent-based mechanochemical coupling, solutes added to the water solvent interfere with the waters of hydrophobic hydration either by decreasing the activity of water or by directly altering the clathrate-like cage of water.

In U.S. Pat. No. 5,226,292, (incorporated herein by reference) the present inventor demonstrated that incorporation of relatively large hydrophobic side chains in monomeric polypeptide units produced a previously unrecognized property in the resulting overall polymer, namely a sensitivity of the inverse temperature transition of the polymer to external pressure. This property is not strictly related to hydrophobicity, as were many prior properties, but required the presence of large hydrophobic side chains. Here "large" means preferably larger in volume than an isopropyl group; i.e., larger than 20 cm$^3$/mole. Even larger hydrophobic groups are preferred (e.g., 100, 500, 1000, or even higher volumes as expressed in cm$^3$/mole). The hydrophobic groups are selected to be sufficiently large and to be present in sufficient extent to provide PdV/dS of at least 0.2° K., preferably at least 1° K., more preferably at least 5° K., and most preferably at least 20° K. (where P=pressure, V=volume, and S=entropy). The patent further provides a method for experimentally determining PdV/dS values. Either increasing the size of hydrophobicity of the hydrophobic groups present or increasing their amount (usually expressed as a mole fraction) in a polymer increases the PdV/dS value. However, knowledge of the exact PdV/dS value for a particular polymer was not required in order to carry out the invention, and estimates of whether any given polymer will be likely to have a desirable baromechanical or barochemical response were readily made by comparison of the amount and type of hydrophobic groups present in a particular polymer. There are no particular upper limits on the size or amount of hydrophobic groups in a polymer of the invention or on the hydrophobicity of the particular substituent as long as the resulting polymer undergoes an inverse temperature transition and has the stated PdV/dS value. These properties and methods apply when designing polypeptides of the present invention which are capable of transducing electrical energy.

The instant application reports the effects of electrical energy on T$_t$ for protein and protein-based bioelastic polymers, particularly of the poly(VPGVG) type and its analogs or co-polymers, and describes how to use these systems to exhibit electrical energy coupled transduction to produce useful work. A model complex polymer poly [0.5 (VPGVG, 0.5(VPGXG)] (referred to herein as copolypeptide II), where X is a glutamic acid residue substituted at its γ-carboxyl group through an amide link to flavin adenine dinucleotide of nicotinamide adenine dinucleotide, was synthesized and studied. Modulation of the polymer's inverse temperature transition by irradiation was monitored by observing phase separation as detected by changes in sample turbidity.

The invention will be described initially using the polymer system that was originally helpful in determining the broader aspects of the invention that are later described herein. However, it will be recognized that this initial description is not limiting of the invention, as these examples can readily be modified using the later-described techniques to provide numerous compositions that have the properties discussed herein and which can be used in the methods and apparatuses described herein.

The first protein polymer system showing electromechanical properties described herein used elastic protein-based polymers of the formula poly[$f$x(VPGXG), $f$v(VPGVG)] where $f$v and $f$x are mole fractions with $f$x+$f$v=1, and X is an amino acid residue having a side chain responsive changes in exposure to electrical energy. As described above, these bioelastomers exhibit inverse temperature transitions in the form of a phase separation in which folding and aggregation of water-soluble polymer chains into more-ordered states of the condensed (coacervate) phase occur on raising the temperature. This inverse temperature transition, while uncommon in the universe of polymers, is common to the bioelastomers described herein and can readily be detected in other polymers by the simple solution/heating scheme described above. Investigations into the polymers of the formula immediately above in which X is 50% glutamic acid and 50% NAD derivative of glutamic acid (see Formula II of Example 1 below), showed that a change in redox potential caused a substantial decrease in the temperature of the transition such that the polymer is above the transition temperature leading to a relatively more hydrophobic form. The volume of the coacervate phase (or of a cross-linked matrix) increases on exposure to electrical energy that induces the hydrophobic hydration, unfolding and disaggregation of the polymer.

The transition temperature is usually selected to be within 20° C. of the temperature of the medium being exposed in order to allow electrically induced effects to occur within a reasonable change in electrical energy. By providing $T_t$ closer to the medium temperature (e.g., less than 10° C., preferably less than 5° C., more preferably less than 2° C.), the system is made more sensitive to changes in electrical energy. Although the inventors do not intend to be limited by the theory of how this expansion takes place, it is believed that water molecules surrounding the hydrophobic side chains of the isomerizing moiety occupy less volume than water molecules in bulk water surrounding the polymer. The capacity to achieve useful mechanical work by polymers of the invention is further illustrated by the calculated volume change for a polymer poly[0.8(GVGVP),0.2(GFGVP)], for example, on going from coacervate phase where hydrophobic associations have largely eliminated waters of hydrophobic hydration to dispersed in water where the hydrophobic moieties are surrounded by water is 80 cm$^3$/mole of mean pentamers, or some 400 cm$^3$/mole of (GFGVP). By incorporating electroresponsive groups that have a similar degree of change in hydrophobicity upon electrical energy exposure, materials exhibiting electrical energy coupled mechanical transduction can be similarly designed to achieve useful mechanical work.

It should be noted that the location of the "X" residue in the polymer as described above is not critical to achieving a response to electrical energy and was made in these examples principally for ease of synthesis. Some variations in properties do occur with substitution of other amino acid residues in the pentameric elastomer unit. The specific location of a side chain in the polymer is not important as long as the bulk properties of the polymer are maintained. However, as taught herein, the magnitude and direction of the bioelastomers response to electrical energy is affected by the location, position, orientation, number, kind and size of the electroresponsive group and other amino acids in the bioelastic unit.

These results illustrate that attachment of one NAD group in approximately forty amino acid residues is sufficient to render electrosensitive the inverse temperature transition of polypeptides, and that isothermal reversible electromodulation of the transition, in this case at 40° C., can be achieved.

Electroresponsive groups are selected to provide a sufficient change in hydrophobicity or polarity and to be present in sufficient extent to provide a shift in the reverse temperature transition of at least 0.2° C., preferably at least 1° C., more preferably at least 5° C., and most preferably at least 20° C. Either increasing the change in hydrophobicity or polarity of the reactive groups present or increasing their amount (usually expressed as a mole fraction) in a polymer increases the shift in the reverse temperature transition. As discussed the shift can be either a decrease or an increase in $T_t$. However, knowledge of the exact degree of shift for a particular polymer is not required in order carry out the invention, and estimates of whether any given polymer will be likely to have a desirable degree and direction of shift in $T_t$ and transduction response is typically determined by comparison of the type and degree of hydrophobic/polar groups present in a particular polymer. There are no particular upper limits on the size or amount of reactive groups in a polymer of the invention or on the hydrophobicity or polarity of the particular electroresponsive substituent as long as the resulting polymer undergoes an inverse temperature transition of the given value. The ratio of electroresponsive groups to monomer residue can range from 1:2 to 1:5000. Preferably the ratio is 1:10 to 1:100. Generally, manufacturing is easier if water-soluble polymers (below the transition temperature) are used. Non-water soluble polymers can be manufactured using organic solvents that in most cases should be removed and replaced with water before use. The upper limit on the number and kind of substituents is also influenced by the ability of the elastic polymer to fold/assemble properly to attain a beta-spiral in the relaxed state. The location of the substituents in the polymer, with respect to the monomer residue side-chain position, is not critical so long as the beta-turn is not prevented from forming in the relaxed state. Preferred positions for the various peptides of the invention are as taught in the patents and pending applications from the laboratory of the present inventors in this area, which have been incorporated by reference.

The superiority of protein-based polymers over that of polymethacrylic acid is demonstrated by comparing efficiencies of achieving mechanical work. The charge-charge repulsion mechanism, represented by polymethacrylic acid, and the salt-dependent collapse of the collagen structure can be compared with the protein-based polymers. A measure of efficiency η can be the mechanical work achieved which is the force $f$ times the displacement, $\Delta L$, divided by the chemical energy, $\Delta\mu\Delta n$, expended in performing the work where $\Delta\mu$ is the change in chemical potential discussed above and $\Delta n$ is the change in moles related to the intrinsic change. For example, $\Delta n$ can be the number of moles of carboxylates (COO$^-$) changed to carboxyls (COOH). The expression for efficiency therefore can be written as $\eta = f\Delta L/\Delta\mu\Delta n$.

Polymethacrylic acid, $[-CCH_3COOH-CH_2-]_n$, utilizes the same (COOH/COO$^-$) chemical couple as the protein-based polymer, poly[0.8(VPGVG),0.2(VPGEG)]. Also, the cross-linked matrices of both can contract to about one-half their extended length and can lift weights that are a thousand times greater than their dry weight such that the numerators, $f\Delta L$ are similar in magnitude (48–50). Where the difference occurs is in the chemical energy required to achieve that work.

For polymethacrylic acid, extension due to charge-charge repulsion is achieved when 50 to 60% of the carboxyl moieties are converted to COO$^-$ and the collapse of the extended state to achieve contraction occurs down to 0 to 10% ionization (48–50). Thus some 40 carboxylates must be protonated per 200 backbone atoms. For $X^{20}$-poly[0.8 (VPGVG),0.2(VPGEG)], only 4 carboxylates per 300 backbone atoms need to be protonated. ("$X_{20}$" indicates that the polymer has been cross-linked with 20 Mrads of gamma radiation.) Thus, the $\Delta n$ is more than 10 times larger for the polymethacrylic acid system. Also the change in chemical potential, $\Delta\mu$, of proton required to achieve those changes in degree or % of ionization is greater for the charge-charge repulsion (polymethacrylic acid) case (51). The change in proton chemical potential to go from 50–60% ionized to 0–10% ionized is some 2 pH units for polymethacrylic acid because of the negative cooperativity of the titration curve (49,51). For the protein-based polymer, the titration curve exhibits positive cooperativity and only the change of a fraction of a pH unit achieves the required change in degree of ionization. The result is that conversion of chemical energy into mechanical work is greater than 10 times more efficient for the $\Delta T^t$-mechanism.

The calculation of comparative efficiencies is as follows. For $\eta_{cc}$, which is the efficiency of charge—charge repulsion mechanism as exemplified by polymethacrylic acid, the factors in the above equation for efficiency are w, where $\Delta L \approx 0.5$ and $f=1000 \times$dry weight, $\Delta n$ is greater than 40 (COO$^- \rightarrow$COOH) per 200 backbone atoms, and $\Delta \mu \approx 2.8$ kcal mol$^{-1}$ ($\Delta \alpha \approx 0.6 \rightarrow \Delta pH \approx 2.0$). For $\eta_{ap}$, which is the efficiency of apolar-polar repulsion free energy mechanism as exemplified by $X^{20}$-poly[0.8(VPGVG),0.2(VPGEG)],for w $\Delta L \approx 0.5$ and $f \approx 1000 \times$dry weight, $\Delta n$ is less than 4 (COO$^- \rightarrow$COOH) per 300 backbone atoms, and $\Delta \mu \approx 0.94$ kcal mol$^{-1}$ ($\Delta \alpha \approx 0.8 \rightarrow \Delta pH \approx 2.0$). The calculated efficiency ratio ($\eta_{cc}/\eta_{ap}$) is greater than 10.

A similar order of magnitude greater change in efficiency is observed for the salt-effected contractions of the polymer $X^{20}$-poly(VPGVG) compared to that of collagen. The complete contraction can readily be achieved on going from 0 to 1 N NaCl for $X^{20}$-poly(VPGVG) and even a change from 0 to 0.15 N NaCl can drive very effective contractions (12). In the collagen case, special salts are required, such as LiBr and NaSCN, and urea can be used. These solutes lower the temperature at which denaturation occurs. In the most characterized case, the use of LiBr, 0 or 0.3 N was the low concentration side and 11.25 N was the high concentration side. Again, over an order of magnitude greater change in chemical potential was required to drive contraction in the collagen model.

From an experimental evaluation of the entropies of the transition, $\Delta S_t (=\Delta H_t/T_t)$, the calculated changes in volume for the transition, $\Delta V_t$, can be obtained, taking into account the different relative heats for the transitions (43), $L=\Delta H_t$.

The experimental work demonstrates how electroresponsive inverse temperature transitions may be achieved in the bioelastic polypeptides of the invention. Electroresponsiveness is achieved by having side chain groups that are electroresponsive, i.e. an electrical energy induced change in the hydrophobicity or polarity of the side chain group occurs, and that participate in a folding/unfolding transition. One design is to have such side chain groups clustered in domains which come into association on folding or which become exposed in unfolding as in a conformational change in which hydrophobic residues are buried in one state and exposed in the other.

Taking these experimental results into consideration, bioelastomers can be rationally designed in order to achieve the desired electrical energy sensitive properties described herein. The teachings of this inventor's previous patents related to bioelastic polymers provides additional information to guide one in the rational design of bioelastomers of the invention when coupled with the teachings of the present specification. The following discussion describes general selection techniques for achieving the embodiments of the invention with a variety of different protein and protein-based bioelastomers.

Using the relative hydrophobicities of the electrical energy-sensitive side chains, it is possible to construct polymers which will exhibit inverse temperature transitions by a systematic, knowledge-based approach. This approach can be used with natural compounds where there is stereochemical regularity, as well as with entirely synthetic molecules, as in the Examples below. Embodiments of the invention can be obtained by making polymers having electroresponsive bioelastic units of the invention interspersed between segments of other biomacromolecules, such as proteins or peptides, nucleic acid, DNA, RNA, lipid, carbohydrates, or stereochemically regular polymers, e.g. poly β-hydroxy alkanoates. Biomacromolecules are chosen to impart additional features such as chemotaxis, cell targeting and adhesion, hydrolase sensitivity, elastic modulus, or drug attachment. Embodiments of the invention can be achieved with polymers that are degradable as well as with polymers that are not so degradable and also with polymers having greater thermal stability. The preferred polymers of the invention are protein and protein-based bioelastomers. Most preferred are those containing bioelastic pentapeptides, tetrapeptides, and nonapeptides.

The regularity of structure of the protein and protein-based electroresponsive polymers of the invention allows optimal arrangement of the structural components for which coupled effects are desired. For example, the electroresponsive side chain can be predictably positioned spatially with respect to the second side chain couple for optimal effect.

Preferred electroresponsive polymers are those which do not occur naturally in their basic form prior to inclusion of the electroresponsive group. Such polymers can be synthetic or recombinant based products. Naturally occurring polymers having an inverse temperature transition can be used as starting material for derivitization to contain electroresponsive side chains. Electroresponsive bioelastic units of the invention can be attached to or interspersed among other types of molecules, which compounds can impart functions to the polymer such as biological activity, chemotaxis, protease, or nuclease susceptibility. Such molecules include peptides, proteins, nucleic acid, DNA, RNA, carbohydrates and lipid chains.

The phenomena of inverse temperature transitions in aqueous systems occurs in a number of amphiphilic systems, commonly polymers, that have an appropriate balance and arrangement of apolar and polar moieties. The polar species contribute to the solubility in water at low temperature, a solubility that results in waters of hydrophobic hydration for the apolar moieties. The waters of hydrophobic hydration, often referred to as clathrate or clathrate-like water, have specific thermodynamic properties: an exothermic heat of hydration (a negative $\Delta H$) and a negative entropy of hydration (6,7). On raising the temperature, by means of an endothermic transition (8), the low entropy waters of hydrophobic hydration become bulk water with a significant increase in solvent entropy as the polymers fold and aggregate, optimizing intra- and intermolecular contacts between hydrophobic (apolar) moieties with a somewhat lesser decrease in polymer entropy than increase in solvent entropy. Such polymers, when their transitions occur between 0° and 100° C., can be used to control events in the aqueous environments that occur in biology. However, transitions that occur at other temperatures can also be used in the practice of the present invention, since the addition of salt or organic solvent to aqueous systems or application of pressure on aqueous systems will cause water to remain liquid at temperature outside the normal liquid-water range. Since systems of the invention can operate under 100 atmospheres of pressure or more, the temperature range can be considerably extended. A preferred temperature range is that of liquid water, wherein there is sufficient bulk water to allow for changes in hydration of chemical groups on the polymer. An upper limit for temperature is the limit above which results irreversible polymer denaturation or racemization that results in a loss of structural regularity of the polymer, which in turn results in a loss of control of polymer activity and transduction efficiency. A lower limit for temperature is the limit below which undesirable effects such as solution solidification and disruptions in polymer structure and regularity occur. A preferred temperature range is from 0° C. to 100° C.

The polypentapeptide poly($Val^1$-$Pro^2$-$Gly^3$-$Val^4$-$Gly^5$), also written poly(VPGVG), is a particularly well-balanced polymer for modification with electroresponsive groups to provide biological utilities as its transition is just complete near 37° C. Below 25° C., it is miscible with water in all proportions where it exhibits a β-turn (see structural formula above) in which there occur hydrogen bonds between the $Val^1$-CO and the $Val^4$-NH moieties (9). On raising the temperature, the polypentapeptide folds into a loose helix in which the dominant interturn hydrophobic contacts involve the $Val^1$-$\gamma CH_3$ moieties in one turn and the $Pro^2$-$\beta CH_2$ moiety in the adjacent turn (10). The loose helical structure is called a dynamic β-spiral and is proposed to be the basis for the entropic elastomeric force exhibited by this material once cross-linked (11). Concomitant with the folding is an assembly of β-spirals to form a twisted filament which optimizes intermolecular contacts.

When poly(VPGVG) is cross-linked, for example, by 20 Mrads of γ-irradiation, an elastomeric matrix is formed which is swollen below 25° C. but which on raising the temperature through the transition contracts with the extrusion of sufficient water to decrease the volume to one-tenth and to decrease the length of a strip of matrix to 45% of its swollen length (2). This thermally driven contraction can be used to lift weights that are one thousand times the dry weight of the matrix. This is called thermomechanical transduction. As will be discussed below, any chemical means of reversibly or irreversibly shifting the temperature of the transition can be used, isothermally, to achieve chemomechanical transduction.

The temperature of the inverse temperature transition of the substituted polypentapeptides described in the following Examples was used to develop a relative hydrophobicity scale as shown in FIG. 1, which contains the apolar side for natural and modified amino acid residues. Introduction of a polar side having protonated/deprotonated chemical couples gives rise to polymer-based chemomechanical transduction. Values for the degree in the shift of $T_t$ are provided for in Table 1 for model side chain groups. The degree of shift in $T_t$ for a coupled electrical energy induced reaction of an electroresponsive side chain group, such as protonation/deprotonation, ionization/deionization, can be determined empirically as taught herein or by using FIG. 1 and Table 1 as a guideline base on the known hydrophobicity or polarity of both states of the electroresponsive side chain. The coupled reaction can be irreversible, such as in addition or dimerization reactions.

A description of the process of designing bioelastomers specifically to provide an inverse temperature transition at any temperature from 0° C. to 100° C. is described below in detail. The specific examples used below to illustrate this process are mostly examples of elastomeric polypentapeptide matrices. However, it will be apparent that the same considerations can be applied to elastomeric tetrapeptide and nonapeptide matrices and to matrices prepared using these elastomeric units in combination with other polypeptide units as described previously for bioelastic materials.

The temperature of inverse temperature transitions can be changed by changing the hydrophobicity of the polymer. For example, make the polypeptide more hydrophobic, as with poly($Ile^1$-$Pro^2$-$Gly^3$-$Val^4$-$Gly^5$), where replacing $Val^1$ by $Ile^1$ represents the addition of one $CH_2$ moiety per pentamer, and the temperature of the transition decreases by 20° C. from 30° C. for poly(VPGVG) to 10° C. for poly(IPGVG) (1). Similarly, decreasing the hydrophobicity as by replacing $Val^4$ by $Ala^4$, i.e., removing the two $CH_2$ moieties per pentamer, and the temperature of the transition is raised by some 40° C. to 70° C.

A major advantage of the bioelastic polypeptides of the invention is the extent to which fine-tuning of the degree of hydrophobicity/polarity and resulting shift in the inverse temperature transition can be achieved. For example, in Example 2 the electroresponsive group is attached to the peptide backbone through the gamma carboxyl group of glutamic acid; however, a decrease in the overall hydrophobicity can be obtained by attachment of the electroresponsive group through the gamma carboxyl group of aspartic acid, which is a shorter homolog of glutamic acid. This replacement is analogous to the replacement of Val by Ala discussed above for protein polymers, and further demonstrates that, in view of the present invention, design concepts previously identified for selecting $T_t$ for other bioelastic polymers applies to the design of electrical energy-reactive bioelastic polymers of the present invention.

Many known compounds are reactive to changes in exposure to electrical energy with well-known reaction products from which to choose in designing bioelastic polymers of the invention. Coupled with the ease of synthesis of peptide units, for example by solid phase peptide synthesis methods, the present specification now provides one skilled in the art with the tools and guidance to design rationally a diverse array of electrosensitive bioelastic polymers of the invention.

The regularity of structure of the protein and protein-based electroresponsive polymers of the invention allows optimal arrangement of the structural components for which coupled effects are desired. For example, the electroresponsive side chain can be predictably positioned spatially with respect to the second side chain couple for optimal effect.

Optimal spatial proximity can be achieved by placing residues adjacent to each other in the backbone (i.e., based on primary sequence) and also by positioning to provide inter-turn proximity. As taught herein, the effect of positioning can be determined both theoretically, based on known structures of model polymers, and empirically as exemplified herein and in the references incorporated herein.

In terms of a generalized hydrophobicity scale, the COOH moiety is more hydrophobic than the $COO^-$ moiety. The transition temperature can be lowered simply by decreasing the pH and raised by increasing the pH of the medium contacting a bioelastomer when a carboxylate group is present (or other group capable of forming an ion upon increasing the pH). If an intermediate temperature is maintained, then a 20 Mrad cross-linked matrix of poly[4 (VPGVG), 1(VPGEG)], that is, a random copolymer in which the two pentameric monomers are present in a 4:1 ratio, where E=Glu, will contract on lowering the pH and relax or swell on raising the pH (12). The temperature of the transition in phosphate buffered saline will shift some 50° C. from about 20° C. at low pH, giving COOH, to nearly 70° C. at neutral pH where all the carboxyls have been converted to carboxylate anions. By choosing a side chain group whose protonation/deprotonation can be modulated, one can in turn modulate the response of the polymer to changes in pH. In addition, the degree of contraction or expansion in response to electrical energy by the polymer containing bioelastic units having an electroresponsive protonizable/deprotonizable group can be modulated by the particular pH of the medium.

For similarly cross-linked poly[4(IPGVG),1(IPGEG)], the temperature of the inverse temperature transition shifts from near 10° C. for COOH to over 50° C. for COO$^-$ (5). For this more hydrophobic polypentapeptide, which contains 4 Glu residues per 100 total amino acid residues, it takes twice as many carboxylate anions to shift the transition to 40° C. as for the less hydrophobic polypentapeptide based on the VPGVG monomer. Thus, it is possible to change the conditions of the transition by varying the hydrophobicity of the region surrounding the group that undergoes the chemical change. Since contraction and relaxation of the bulk polymer is dependent on the sum of all local thermodynamic states, sufficient control is possible merely by controlling the average environment of, for example, ionizable groups, such as by changing the percentage of monomers present in a random (or organized) copolymer.

When the pH is lowered (that is, on raising the chemical potential, m, of the protons present) at the isothermal condition of 37° C., these matrices can exert forces, $f$, sufficient to lift weights that are a thousand times their dry weight. This is chemomechanical transduction, also called mechanochemical coupling. The mechanism by which this occurs is called a hydration-mediated apolar-polar repulsion free energy and is characterized by the equation $(\delta\mu/\delta f)_n<0$; that is, the change in chemical potential with respect to force at constant matrix composition is a negative quantity (13). Such matrices take up protons on stretching, i.e., stretching exposes more hydrophobic groups to water which makes the COO$^-$ moieties energetically less favored. This is quite distinct from the charge-charge repulsion mechanism for mechanochemical coupling of the type where $(\delta\mu/\delta f)_n>0$ and where stretching of such matrices causes the release of protons. The hydration-mediated apolar-polar repulsion mechanism appears to be an order of magnitude more efficient in converting chemical work into mechanical work.

It may be emphasized here that any chemical means of changing the mean hydrophobicity of the polymer, such as an acid-base titratible function, dephosphorylation/phosphorylation, reduction/oxidation of a redox couple, etc., can be used to bring about contraction/relaxation. At least one of the coupled reaction states of the electroresponsive side chain will be achieved upon a change in exposure to electrical energy. Fine tuning of the transitions can be achieved by employing the hydrophobicity or induced chemical changes on the side chains of certain amino acids, preferably one of the 20 genetically encoded amino acids or a derivative thereof. Examples of electrical energy induced reactions of side chain groups include ionization, deionization, oxidation, reduction, amidation, deamidation, isomerization, dimerization, hydrolysis, and addition.

Fine-tuning of the degree of contraction/expansion as well as transduction to non-mechanical free energies can be achieved by the addition of other reactive groups to the bioelastic polymers of the invention. Such polymers are embodiments of the present invention. Furthermore, amino acid monomer units are readily modified to further expand the set of available reactions for fine-tuning. For example, a sulfate ester of Ser can be added in which sulfate ionizations will occur at a pH outside the range experienced by carboxylate groups. A change in the isomerization state of azobenzene attached to an amino acid by reaction of a functional group in the modifying moiety and a functional group in an amino acid side chain is also effective.

As discussed, electrical energy induced reactions can change the hydrophobicity or polarity of an electroresponsive side chain attached to an amino acid side chain. As the electroproducts can be quite varied, reactions are available to one rationally designing polymers of the invention so that either a lowering of the value of $T_t$ or an increase in the value of $T_t$ can be obtained. For example, reduction of nicotinamide dramatically lowers the value of $T_t$ leading to electrically driven folding, whereas oxidation of nicotinamide would increase the value of $T_t$.

As taught herein polypeptides or proteins with the correct balance of apolar (hydrophobic) and polar moieties become more-ordered on raising the temperature because of hydrophobic folding and assembly. This process is called an inverse temperature transition. For some of the polypeptides the inverse temperature transition is a reversible phase transition with the formation of a more-dense, polypeptide-rich, viscoelastic phase on raising the temperature. When the viscoelastic phase is cross-linked, elastic matrices are formed which, on raising the temperature through the temperature range of the inverse temperature transition, contract and in doing so lift weights that can be a thousand times the dry weight of the matrix. These matrices can perform useful mechanical work on raising the temperature. Such elastic matrices are referred to as zero order molecular machines of the inverse temperature transition ($T_t$) type.

Figure 3:
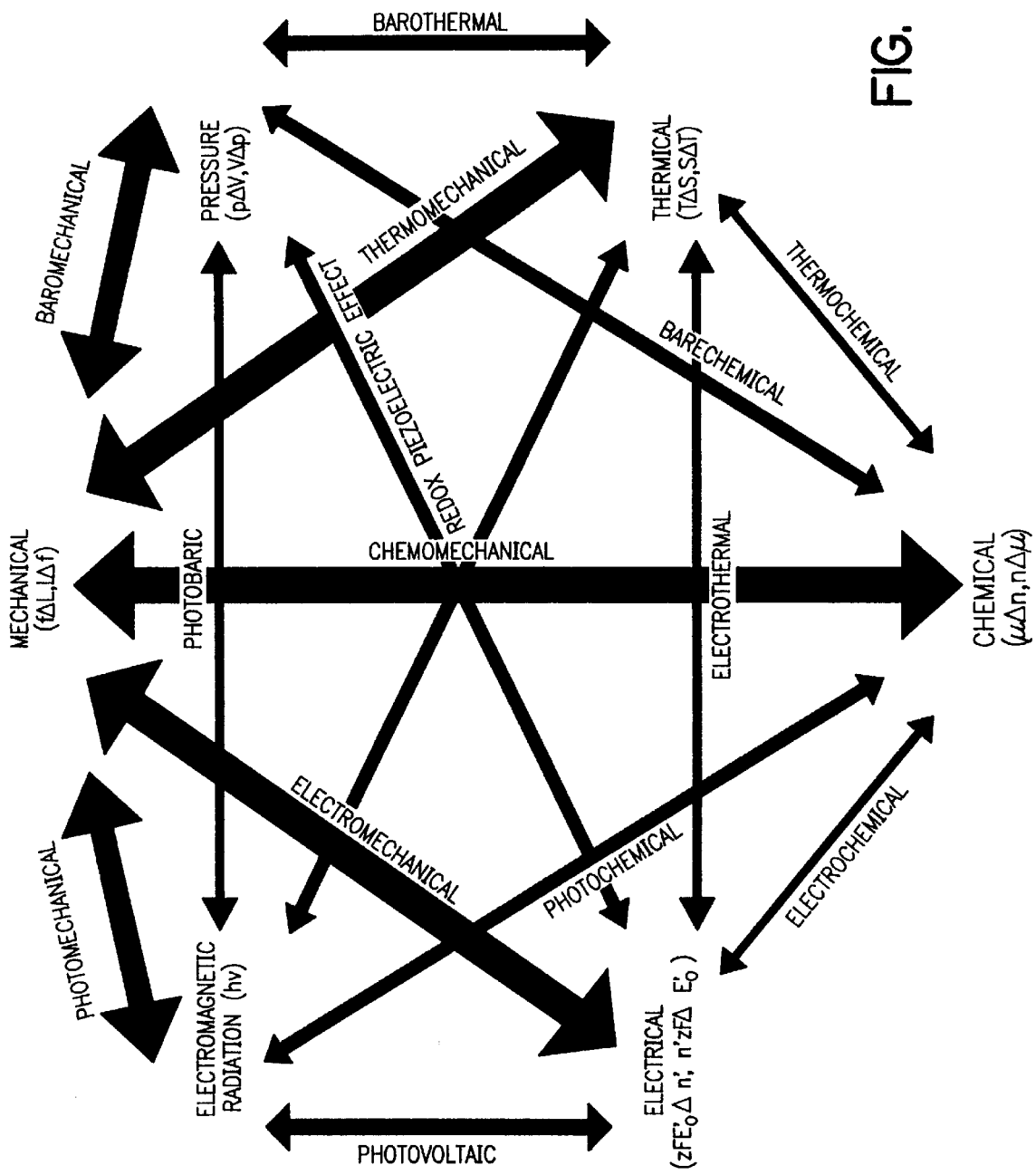
FIG. 3 is a schematic depicting energy transductions of the $T_t$ type.

It is possible, without a change in temperature, to drive the inverse temperature transition of hydrophobic folding and assembly by each energy source that can lower the value of $T_t$, that is, to lower the temperature range over which the inverse temperature transition occurs. Four different energy sources have been found to change the value of $T_t$. Stated in terms of free energy transductions, these are chemomechanical, baromechanical, electromechanical and photomechanical transduction. With a polymer having an attached side chain group that can be reduced or oxidized either chemically or by means of an electrical potential, a chemical change can markedly change the value of $T_t$. In a similar manner, the presence of a chromophore, which on absorption of light produces a long-lived change in the polarity of the chromophore, can change the value of $T_t$. This general process is called the $\Delta T_t$-mechanism of free energy transduction. Each of these energy inputs can reversibly drive hydrophobic folding or unfolding, as the case may be, with the performance of useful mechanical motion. As such the designed proteins are molecular engines, and they may also be called first-order molecular machines of the $T_t$-type. FIG. 3 depicts first-order energy type transductions as those that entail all of the pairwise energy conversions involving the mechanical apex.

Changing the composition of the protein-based polymer systematically changes the transition temperature. Furthermore, the intrinsic chemical change of changing the degree of ionization of a functional side chain in the polypeptide also changes the temperature at which the inverse temperature transition occurs, which is equivalent to changing composition without synthesis of a new polymer. The cross-linked viscoelastic phase of such a polypeptide isothermally exhibit a pH-driven contraction capable of doing useful mechanical work. In general, such an elastic matrix, in which chemical energy or any other energy source can change the temperature at which the inverse temperature transition occurs and can thereby be caused to contract and perform useful mechanical work, is called a first order molecular machine of the $T_t$ type. The work performed is the direct result of hydrophobic folding and assembly. The $T_t$-type first order energy conversions are those coupled to mechanical work.

Any energy input that changes the temperature, $T_t$, at which an inverse temperature transition occurs can be used to produce motion and perform mechanical work. Chemically-driven hydrophobic folding can result in motion and the performance of mechanical work, i.e., chemomechanical transduction. Electrochemically driven, pressure release-driven, and photo-driven hydrophobic folding result in electromechanical, baromechanical, and photomechanical transductions, respectively. Bioelastic polymers capable of transducing these energies are examples of first-order molecular machines of the $T_t$-type. Electromechanical transduction is achieved using polymers of the invention that have an electroresponsive moiety, such as an attached nicotinamide.

Different energy inputs, each of which can individually drive hydrophobic folding to produce motion and the performance of mechanical work, can be converted one into the other (transduced) by means of the inverse temperature transition with the correctly designed coupling and $T_t$ value, as taught herein. Electrically (reduction) driven hydrophobic folding can result in the performance of chemical work, e.g. the uptake (or release) of protons, i.e., electrochemical transduction. Controlled hydrophobic folding results in additional transductions: electrothermal, baroelectrical, photovoltaic, thermochemical, photothermal, barothermal, barochemical, photobaric, and photochemical. Bioelastic polymers of the invention capable of electrothermal, baroelectrical, and electrochemical transductions are examples of second-order molecular machines of the $T_t$-type.

In addition to mechanical coupled transduction, bioelastic polymers capable of $T_t$-type second order energy conversions such as electrochemical, electrothermal, and baroelectrical, are now possible in light of the teachings of the present specification. Second order energy conversions of the $T_t$-type are those not coupled directly to mechanical energy, for example, electrochemical transduction as taught herein, or barochemical transduction as taught in U. S. Pat. No. 5,226,292. Though these transductions utilize the hydrophobic folding and assembly capacity of the elastic matrix, mechanical work is not one of the pair of energies being interconverted. As a further example of a $T_t$-type second order energy conversion, consider a swollen matrix of unfolded polypeptides containing both an oxidized component of a redox couple, e.g., N-methyl nicotinamide, and the charged moiety of a chemical couple, e.g. (COO$^-$), with the composition of the protein-based polymer such that $T_t$ is just above the operating temperature. Under these circumstances, either lowering the pH to convert the COO$^-$ to COOH or the reduction of the nicotinamide, the oxidized prosthetic group (redox couple), would lead to hydrophobic folding and assembly. If the oxidized prosthetic group were reduced, then the resulting folding would be expected to shift the pKa of the carboxyl moiety, and under the proper conditions the chemical result would be an uptake of protons (a decrease in proton chemical potential). If, on the other hand, the pH were lowered and the carboxylate anion were protonated, then the electrochemical potential of the oxidized prosthetic group would be expected to shift in favor of reduction and the electrical result could be the uptake of electrons.

Either of these scenarios are designated as electrochemical transduction. Both utilize hydrophobic folding, but the energy produced or the work performed is not mechanical in nature. The elastic matrix so designed to achieve electrochemical transduction is in our designation a second order molecular machine of the $T_t$-type. This is but one example of electrochemical transduction. One skilled in the art can now rationally design bioelastic polymers that undergo electrical energy coupled second order transductions of the $T_t$-type.

Depending on the work, type of transduction, or polymer activity desired, the type of couple for a second side chain couple includes ionization/deionization, oxidation/reduction, protonation/deprotonation, cleavage/ligation, phosphorylation/dephosphorylation, amidation/deamidation, etc., a conformational or a configurational change, e.g. cis-trans isomerization, an electrochemical change, e.g. pKa shift, emission/absorbance, or other physical change, e.g. heat energy radiation/absorbance. A preferred change that takes place in an aqueous environment is a chemical change. A preferred chemical change is a pKa shift. As depicted in FIG. 3, second-order type free energy conversion are those ten pairwise energy conversions which do not involve the mechanical force apex. These energy conversions utilize the inverse temperature transitions, that is, the hydrophobic folding and assembly transitions, but they do not require the production of useful mechanical motion. These energy conversions (exclusive of thermomechanical transduction) include among others those energy inputs which drive hydrophobic folding or unfolding to result in the uptake or release of heat as when the arrow ends at the thermal apex of FIG. 3. They can include changes in the states of coupled functional moieties as when the arrow ends at the chemical, electrical, pressure or electromagnetic radiation apices. Electroresponsive polymers of the invention that transduce energy utilizing the inverse temperature transition but do not directly produce motion from the folding are referred to as second-order molecular machines of the $T_t$-type where again $T_t$ is to indicate the use of the inverse temperature transition as the mechanism for transduction.

An example of an electrochemical transduction occurs when, for instance, an oxidation or reduction reaction of an electroresponsive side chain group attached to a bioelastic polymer produces a change in chemical energy seen as the release or uptake of a proton from a second side chain functional moiety, e.g. an ammonium or carboxylate moiety. If the reaction is a reduction which lowers $T_t$ and drives hydrophobic folding, then a suitably coupled carboxylate moiety will have its pKa raised such that it can take up a proton to become part of the hydrophobically folded structure.

As an example, the composition of the bioelastic polymer of the invention capable of electrochemical transduction can be of the formula, or contain a segment of the formula, poly[$f_x$(VPGXG),$f_y$(VPGVG),$f_z$(VPGZG)] where $f_x$, $f_y$, and $f_v$ are mole fractions with $f_x+f_y+f_z=1$, X represents the electrical energy-reactive amino acid residue, and Z represents an amino acid residue having a side chain capable of undergoing reversible chemical change in an aqueous environment.

It is also possible to exert fine control over the transition from a relaxed to a contracted state (or vice versa) by controlling the average environment in which the various functional groups undergoing transition are located. For example, the hydrophobicity of the overall polymer (and therefore the average hydrophobicity of functional groups present in the polymer) can be modified by changing the ratio of different types of monomeric unit, as previously exemplified. These can be monomeric units containing the functional group undergoing the transition or other monomeric units present in the polymer. For example, if the basic monomeric unit is VPGVG and the unit undergoing transition is VPGXG, where X is a amino acid reside modified to have an electroresponsive side chain, either the ratio of VPGVG unit to VPGXG units can be varied or a different structural unit, such as IPGVG, can be included in varied amounts until the appropriate transitions temperature is achieved.

In general, selection of the sequence of amino acids in a particular monomeric unit and selection of the required proportion of monomeric units can be accomplished by an empirical process that begins with determining (or looking up) the properties of known bioelastomers, making similar but different bioelastomers using the guidance provided in this specification, and measuring the transition temperature as described herein and in the cited patents and patent applications. Preferably, however, one uses tables of relative hydrophobicity of amino acid residues (either naturally occurring or modified) to compute the transition temperature without experimentation. For example, see Y. Nozaki and C. Tanford, *J. Biol. Chem.* (1971) 246:2211–2217, or H. B. Bull and K. Breese, *Archives Biochem. Biophys.* (1974) 161:665–670, for particularly useful compilations of hydrophobicity data. For example, a rough estimate can be obtained of the likely transition temperature by summing the mean hydrophobicities of the individual amino acid residues, or their side chain modified forms, in the monomeric units of the polymer and comparing the result to the sum obtained for polymers having known transition temperatures.

More accurate values can be calculated for any given polymer by measuring transition temperatures for a series of related polymers in which only one component is varied. For example, polymers that mostly contain VPGVG monomers with varying amounts of VPGXG monomers (e.g., 2%, 4%, and 8% X) can be prepared and tested for transition temperatures. The test merely consists of preparing the polymer in uncrosslinked form, dissolving the polymer in water, and raising the temperature of the solution until turbidity appears, which indicates the precipitation of polymer from solution. If the transition temperatures are plotted versus the fraction of VPGXG monomer in the polymer, a straight line is obtained, and the fraction of VPGXG necessary for any other desired temperature (within the limits indicated by 0% to 100% of the VPGXG monomer) can be obtained directly from the graph. When this technique is combined with the rough estimating ability of hydrophobicity summing as described above, any desired transition temperature in the range of liquid water can be obtained.

Bioelastomeric materials provide a chemically modulable polymer system as part of which there can be a controlled rate of presentation of more polar species such as the carboxylate anion. By the mechanism described above where $(\delta\mu/\delta f)_n < 0$, the pKa of a carboxyl moiety in a polymeric chain can be increased by increasingly vicinal hydrophobicity (13,15).

As noted above, hydrophobic hydration is an exothermic process. Accordingly, the reverse process of the inverse temperature transition, which involves the destruction of the waters of hydrophobic hydration in order for hydrophobic association to occur, is an endothermic process. Using the same elastic protein, poly[0.8(VPGVG),0.2(VPGEG)], as used in the stretch experiment discussed above, the endothermic heat of the inverse temperature transition is approximately 1 kcal/mole of pentamers at low pH where all of the Glu(E) side chains are COOH. When the pH is raised to 4.5 where there are approximately two COO⁻ moieties per 100 residues, and less than a 20° C. increase in the value of $T_t$, the endothermic heat of the transition has been reduced to almost one-fourth. It appears that nearly three-fourths of the thermodynamically measurable water of hydrophobic hydration has been destructured during the formation of two COO⁻ moieties. This is consistent with the above proposed mechanism; competition between apolar and polar species for hydration has resulted in two carboxylate anions in 100 residues effectively destructuring a majority of the water of hydrophobic hydration.

Although the discussion above is general to the phenomenon of controlling inverse temperature transitions in bioelastomers, regardless of whether those materials have the electrical energy coupled transduction properties of the invention, it will be recognized that the same discussion is relevant to varying the inverse temperature transition of compositions of the invention. Controlling the value of $T_t$ is a dominant means whereby the folded and assembled states of protein and protein-based bioelastic polymers are controlled in order to achieve function. As previously discussed, polymers of the invention incorporate electroresponsive side chains of a sufficient number and of a reaction couple type to provide the desired electrical energy-sensitive effects. Providing a polymer with the electroresponsive effects of the invention, however, does not eliminate the other properties of these polymers. Accordingly, it is possible to achieve the various mechanochemical and thermochemical properties that have been previously described in, for example, bioelastic materials by providing a polymer that contains functional groups in addition to those required for electrical energy sensitivity. As taught herein, selection of appropriately sensitive second side chains, e.g. light energy sensitive side chains or large hydrophobic side chains (for pressure sensitivity), allow the potential free energy transductions between electrical energy and chemical, thermal, pressure, or light energy to occur using compositions of the invention. A polymer will have the inherent thermal and mechanical properties it merely has the polymer backbone and the required inverse temperature transition. By providing side chains reactive to changes in electrical energy will allow electrical energy modulation to occur.

Figure 2:
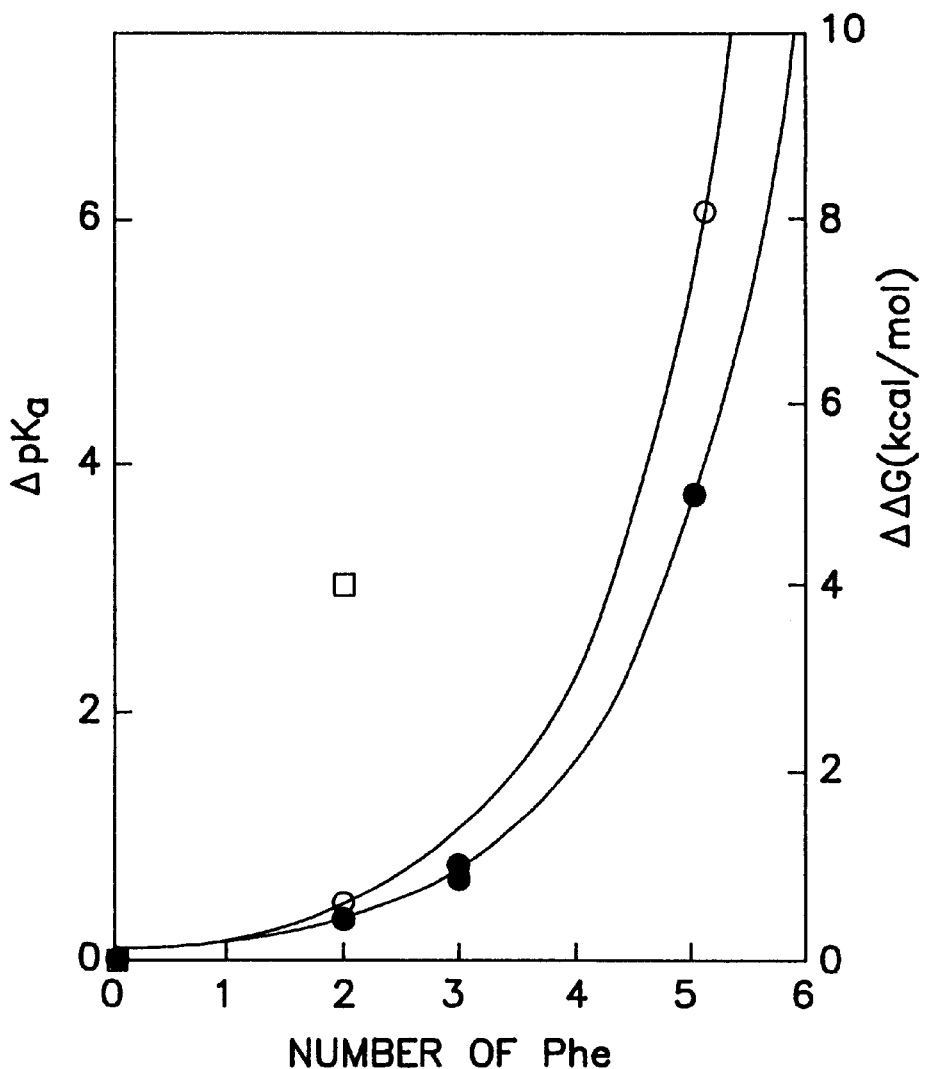
FIG. 2 is a graph showing the non-linear relationship between bioelastomeric unit hydrophobicity (exemplified by the number of phenylalanine residues present in the unit) and hydrophobic-induced pKa shift.

As discussed above, an unexpected relationship was observed between hydrophobicity and hydrophobic-induced pKa shifts. This phenomenon can be taken advantage of to allow "poising" of the polymer to enhance the efficiency of electrical energy transduction. Using proteins of the structure poly[$f_y$(IPGVG), $f_x$(IPGXG)] where $f_x$ is varied from 1 to 0.06 and for X=E(Glu), D(Asp) or K(Lys), it has been possible to delineate electrostatic-induced from hydrophobic-induced pKa shifts. Larger pKa shifts can be obtained in water when hydrophobic-induced than when electrostatic-induced (Reference 34, which is incorporated herein by reference). To determine how large the hydrophobicinduced pKa shifts can be, a series of polytricosamers, poly(30 mers) based on a series of six GVGVP repeats, were synthesized in which up to five of the twelve Val residues per 30 mer were replaced by the more hydrophobic Phe residues. When the five Phe residues were optimally placed with respect to the Glu or Asp residue consistent with the β-spiral structure of poly(VPGVG), pKa shifts as large as 3.8 were observed for Glu(E) and as large as 6.1 were observed for Asp(D). For the Asp case when only two of the five Phe replacements were included in the polytricosamer, the pKa shift is 0.4 and when the other three of the five Phe replacements were present, the pKa shift was 0.7. If the process were simply the displacement of higher dielectric water by the lower dielectric Phe residues, the substitutions of the first two and of the second three Val residues by Phe should be essentially additive, that is, 0.4+0.7=1.1, but instead the shift is 6.1. The magnitude of the shift is very non-linear with respect to the number of Phe (hydrophobic) residues present in the polymer (FIG. 2).

Regarding hydrophobic-induced pKa shifts, an increase in pKa occurs for a carboxyl group upon an increase in hydrophobicity of the bioelastic unit. For amino groups and histidine a decrease in pKa occurs with increasing hydrophobicity. The direction of the pKa shift depends on which state of the group is more hydrophobic.

A comparison of pKa shift of polymer poly (GEGFP GVGVP GVGVP GVGVP GFGFP GFGFP) and poly (GEGFP GVGVP GVGFP GFGFP GVGVP GVGFP) unexpectedly shows that the latter polymer gives a greater pKa shift (Reference 52, which is incorporated herein by reference). The effect is unexpected since on the basis of primary structures, the Glu residues in the first polymer would experience greater hydrophobicity and would be expected to give the larger pKa shift. Only when the proper 3-dimensional conformation, in this case β-spiral folding, is taken into account does the spatial proximity become apparent, and the Glu-Phe proximity provides the understanding for the larger pKa shift exhibited by the latter polymer. Thus with regard to protein engineering of electroresponsive bioelastic polymers of the invention, increasing the 3-dimensional proximity of hydrophobic residues to either the electroresponsive group or the second side chain couple, in the case where either or both can undergo a pKa shift, will increase the magnitude of the pKa shift. The hydrophobicity-induced pKa shift effect exemplifies how to make and design polymers of the invention to fine-tune and control the electroresponsiveness of the polymers. The regularity of the polymer structures of the invention allows predictability of structure during polymer design, a feature not enabled by previously available random structure polymers such as polyacrylamides.

Mean residue hydrophobicities of a polymer can be calculated using the hydrophobicity scale for amino acids (Table 1) and the method of Urry et al. (44 and 52, which are both incorporated herein by reference).

The unexpected non-linearity of hydrophobic-induced pKa shifts is depicted in FIG. 2 for polymers containing a protonizable residue, e.g. glutamic acid, aspartic acid, or histidine, with increasing numbers of hydrophobic phenylalanine residues. Effects such as pKa shift not only increase with increasing hydrophobicity designed into the polymer, but increase in a non-linear way. Enhancement of other effects can be elicited by poising including expansion/contraction, oxidation/reduction, ionization/deionization, salt uptake/release and light-energy coupled transductions.

Preferred electroresponsive moieties are those that can be attached, positioned and oriented along the polymer. A preferred electroresponsive reaction that results in a change in hydrophobicity or polarity of the side-chain is a dinucleotide, e.g., NAD or FAD. Also preferred are analogs of the above electroresponsive molecules, particularly their naturally occurring breakdown products that retain electroresponsiveness.

Cross-linking of a polymer solution to form an elastic matrix can be performed using various cross-linking process, e.g. chemical, enzymatic, irradiative. U.S. Pat. No. 4,589,882, incorporated herein by reference, teaches enzymatic cross-linking by synthesizing block polymers having enzymatically crosslinkable units. If radiation is used to cross-link polymer embodiments of the invention, the side chain substituents responsible for the $T_t$ effect are chosen so as to be non-reactive or minimally reactive to the cross-linking irradiation.

The electroresponsive materials of the invention can be used in a variety of different methods, apparatuses that perform work, and devices that indicate changes in electrical energy or transduce other types of free energies. It will be apparent that useful mechanical and/or chemical work can be obtained from the expansions and contractions of the compositions of the invention with changes in electrical energy and that such work can be used in a variety of situations, particularly in sealed systems or systems susceptible to contamination and that therefore are difficult to mechanically manipulate from outside the system. The following examples of methods, apparatuses, and devices are only a few of the many possible variations.

It is understood that the limitations pertinent to the electroresponsive bioelastic polymers of the invention also pertain to compositions, apparatuses and machines containing those polymers and to methods of making of those polymers. For example, preferred compositions are those containing a bioelastomeric polymeric material containing bioelastomeric repeating units selected from the group consisting of bioelastic pentapeptides, tetrapeptides, and nonapeptides, wherein at least a fraction of said units contain an amino acid residue having an electroresponsive side chain. And, for example, useful compositions for Tt-type second order energy transductions include those wherein the bioelastic polymer further contains at least a fraction of bioelastomeric repeating units having a second amino acid residue with a side chain capable of undergoing a chemical change.

One method of the invention produces mechanical work by changing exposure to electrical energy on a composition of the invention as described above. The composition, usually a polymer in an aqueous environment surrounded by bulk water so that water can move into and out of the polymer as transitions occur, is constrained so that expansion and/or contraction of the polymer produces mechanical work. One manner of providing the desired electrical energy change on the composition is to provide the composition in an aqueous environment and to change its electrochemical potential. The change can be, for example, an oxidation/reduction of a thio group or coordination of a ligand with the iron atom of heme etc. Either macro or micro methods of electrical energy exposure are known in the art and are suitable for electrical energy delivery.

As an example, an apparatus for producing mechanical work can be prepared that contains a polymer or other material of the invention that is constrained so that expansion or contraction of the polymer will produce mechanical work. When the electropotential of the polymer is changed, the polymer will expand or contract to produce the desired work. The composition is prepared in the form of a strip, with one end of the strip being attached to a fixed location in a container and the other end being attached to an object being moved which could be a weight, a lever, switch, or other mechanical operation. Depending on the electroresponsive group provided in the polymer a change in the electrical energy can either cause the object to be lowered or to be raised as the supporting strip contracts. The object may be a piston such that expansion or contraction of the polymer in response to electrical energy causes movement of the piston to produce useful mechanical work.

When functional groups capable of undergoing reversible chemical change are included in the electroresponsive compositions as discussed above, chemical changes can be caused to occur in systems merely by changing the electrical energy on the system. For example, if the chemical change is protonation, a pH change can be caused in the environment surrounding a composition of the invention by changing the electrical energy exposure to the composition, which effects a change in the contraction/expansion of the composition such that a change in the pKa of the composition and a resulting change of pH in the environment results. This method can readily be embodied in an apparatus.

In one embodiment, electrical energy can be measured through changes in pH of the aqueous medium surrounding a composition of the invention as the aqueous medium undergoes changes in exposure to electrical energy. As the electrical energy exposure on the composition changes and results in either a contraction or expansion of the composition, pKa changes in the composition will cause pH changes in the surrounding water. It is merely necessary to have the scale of the pH meter calibrated in units of electrical energy to have the system provide an electrical energy reading at a remote location.

Compositions of the invention are also useful in situations where contraction beyond that applied through mechanical means is desired. For example, one useful application for the composition of the invention is therefore as surgical sutures, particularly for microsurgical procedures. Sutures made from compositions of the invention can be used in anastomosis, for example, and with subsequent application of electrical energy contract (irreversibly if the appropriate electroresponsive group is present in the polymer) and tighten to the degree desired. Particularly preferred for this purpose are materials based on elastomeric pentapeptide, tetrapeptide, and nonapeptide monomers as described herein, as these material have already been demonstrated to be biocompatible. See the various patents and patent applications listed above dealing with biocompatible uses of these materials and the formation of these materials into such devices. Although these prior patents and applications have not been concerned with electroresponsive polymer compounds, they provide considerable guidance on biocompatibility and on manufacturing of bioelastomers to obtain useful structural and surface features for biomedical uses.

Membranes comprised of bioelastic polymers are another useful embodiment of the invention that provides an alternative to "heat-shrinking" as means of achieving a tight sealing of a membrane or sheath across an area or around an object. The application of electrical energy of a particularly type or intensity to a membrane made from bioelastic polymers can induce contraction of the polymer resulting in shrinking of the membrane or sheath. The shrinking can be reversible or irreversible depending on the choice of reactive group as taught herein.

One or more of the peptide bonds can be optionally replaced by substitute linkages such as those obtained by reduction or elimination. Thus, one or more of the —CONH— peptide linkages can be replaced with other types of linkages such as —CH$_2$NH—, —CH$_2$S—, CH$_2$CH$_2$—, —CH=CH— (cis and trans), —COCH$_2$—, —CH(OH)CH$_2$— and —CH$_2$SO—, by methods known in the art, for example, see Spatola, A. F. (1983) in *Chemistry and Biochemistry of Amino Acids, Peptides and Proteins* (B. Weinstein, ed.) Marcel Dekker, New York, P. 267 for a general review. Amino acid residues are preferred constituents of these polymer backbones. Less preferred constituents are amino acid homologs. Although electroresponsive groups and second side chain reaction couple groups are preferably attached using known amino acid and protein chemistry methods to functional reactive groups on amino acid chain side chains, the linkage is not critical so long as it does not hinder the electroresponse or second side chain couple reaction, allows the desired positioning of the side chains to achieve effects such as poising, and does not disrupt the bioelastic units structure necessary to achieve an inverse temperature transition. Of course, if desired a linkage can be chosen to modulate either side chain response.

Of course, if backbone modification is made in the elastomeric units, then suitable backbone modifications are those in which the elasticity and inverse temperature transition of the polymer is maintained.

The choice of individual amino acids from which to synthesize the elastomeric units and resulting polypeptide is unrestricted so long as the resulting structure comprises elastomeric structures with features described, for example, in U.S. Pat. Nos. 4,474,851 and 5,064,430, particularly β-turn formation, and incorporate electroresponsive side chains as disclosed in the present application.

As disclosed in earlier U.S. Patents, additional properties, e.g. strength, specific binding, are imported to bioelastomeric materials by compounding the repeating elastic units to a second material with greater strength or with the desired property as disclosed, in U.S. Pat. Nos. 4,474,851 and 5,064,430.

By biological compatible is meant that the material in final form will not harm the organism or cell into which it is implanted to such a degree that implantation is as harmful or more harmful than the material itself.

Such compounding can be oriented in the backbone of the polymer by preparing copolymers in which bioelastic units that form β-turns are interspersed among polymer units providing a desired property e.g. cell adhesion sequences containing Arg-Gly-Asp.

This new type of biomaterial can be designed for a diverse set of applications, thereby complementing and extending the uses for bioelastic materials described in the numerous patents and patent applications by this inventor. Electrical energy induced changes in the $T_t$ of a target bioelastomeric peptide allows for non-invasive methods of effecting a desired result. For example, a drug delivery matrix (see this inventor's United States patent application Ser. No. 07/962, 608, filed Oct. 16, 1992, which is incorporated herein by reference) comprised of an electrosensitive bioelastic polymer of the present invention which releases its drug upon a change in electrochemical potential finds use, for example, in tissue culture where the delivery of drugs or other factors to cells at a desired point in time can be achieved without necessitating invasive procedures that would increase the chance of culture contamination or a change in other culture conditions. Similarly, drug delivery can occur in vivo by administration of a drug-impregnated bioelastic matrix that is designed to change $T_t$ and contract and release its drug in response to electrical energy. Controlled drug release and/or degradation of the drug-impregnated bioelastic matrix can be achieved by incorporating electroresponsive side chain groups that obtain the properties of side-chain groups taught in United States patent application Ser. No. 07/962,608, such as functional groups that are susceptible to hydrolysis upon change in electrochemical potential. The drug-impregnated or containing matrix can be of a sponge-type or of an envelope type. Drug delivery can be extended to controlled pesticide or herbicide release. These are but some examples of the use of the bioelastic peptides of the invention for the transduction of (change in) electrical energy to useful mechanical work.

This inventor's U.S. Pat. No. 5,032,271, describes an apparatus containing a bioelastic polymer that is capable of desalination sea water or brackish water with the assistance of an applied mechanical force, converting mechanical to chemical energy. The electrical energy-reactive polymers of the present invention provide an apparatus for desalination that can be driven by electrical energy. A desalinator involves an expandable container, having a water fill port and a drain port, and containing a bioelastic polymer of the invention (capable of reversible reaction) in a relaxed state in salt water. Upon a change in exposure of the polymer to electrical energy, the polymer expands. Expansion of the polymer exposes hydrophobic groups and the polymer uptakes water as the exposed hydrophobic groups become surrounded with clathrate-like water. Since the uptake of ions from the solution is not favored by the hydrophobicity of the polymer, the water taken up is lower in ions than the starting salt water. The excess water which is high in salt is drained from the container while the polymer stretches. By returning the exposure of electrical energy to the starting state, the polymer will contract causing an extrusion of water which is lower in salt concentration. The process can be repeated using with the reversibly responding polymer to until the salt water is effectively desalted. This is but another example of how the present invention extends the applications of previously known bioelastic polymers.

The invention now being generally described, the same will be better understood by reference to the following examples, which are provided for purposes of illustration only and are not to be considered limiting of the invention unless so specified.

EXPERIMENT 1

Synthesis of Appropriate Protein-Based Polymers

The pentapeptides required for the synthesis of these polymers will be synthesized as previously described in Urry et al. "Syntheses, Characterizations and Medical Uses of the Polypeptide of Elastin and Its Analogs", In *Biocompatibility of Tissue Analogues*, (D. F. Williams, Ed.), CRC Press, Inc. Boca Raton, Fla., 89–116(1985) and Urry et al., :Chemical Potential Driven Contraction and Relaxation by Ionic Strength Modulation of an Inverse Temperature Transition", *J; Am. Chem. Soc.,* 110:3303–3305 (1988).

Boc-GVGVP-ONp(0.67 mole) and Boc-GFGVP-ONp (0.33 mole) are to be deblocked together using TFA, and one molar solution of TFA salt in dimethyl sulfoxide (DMSO) is polymerized for 14 days using 1.6 equiv. of NMM as base. At the end of that time, the polymer is dissolved in water and dialyzed against 3500 mol. wt. cut-off dialysis tubing and lyophilized. The polymer is redissolved in water, base treated with 1 N NaOH, dialyzed against 50 kD mol. wt. cut-off and lyophilized to obtain poly[0.67(GVGVP)0.33 (GFGVP)], as polymer I.

Boc-GVGVP-ONp(0.57 mole),Boc-GFGVP-ONp(0.33 mole) and Boc-GE(OCHx)GVP-ONp(0.1 mole) are deblocked and polymerized. The polymer is dialyzed in 3500 mol. wt. cut-off dialysis tubing and lyophilized. The glutamic acid side chain protection (OCHx) is deblocked using HF:p-cresol (90:10,v/v) for 1 hour at 0° C. The polymer is washed with ether and redissolved in water. The pH of the solution is adjusted to pH 10 and stirred overnight at 4° C. The pH is adjusted to pH 6, dialyzed in 50 kD mol. wt. cut-off dialysis tubing and lyophilized to obtain poly [0.57(GVGVP)0.33(GFGVP) 0.1 (GEGVP)], as polymer II.

The synthesis of pentadecamer is by 5+(5+5) strategy. Boc-GVGFP-OBzl is deblocked with HCl/dioxane and coupled to BOC-GE(OCHx)GVP-OH using 1-ethyl-3-[3-(dimethylaminopropyl]carbodiimide hydrochloride (EDCI) with hydroxybenztriazole (HOBt) to give Boc-GE(OCHx) GVPGVGFP-OBzl. The decapeptide benzylester is deblocked and coupled to Boc-GVGFP-OH in the presence of EDCI and HOBt to obtain Boc-GVGFPGE(OCHx) GVPGVGFP-OBzl. This is hydrogenated to free acid which is further converted to the p-nitrophenyl ester (ONp) on reacting with bis(p-nitrophenyl) carbonate. The Boc group is removed, and the pentadecamer is polymerized and treated as compound II to obtain poly[GVGFPGEGVPGVGFP], as polymer III. This polymer is useful in studying the effect of increasing the proximity of F to E and of the increased Phe content.

Boc-GVGVP-ONp (0.57 mole) Boc-GFGVP-ONp (0.33 mole) and Boc-GK(2-Cl-Z)GVP-ONp (0.1 mole) is deblocked, polymerized, dialyzed in 3500 mol. wt. cut-off and lyophilized. The lysine side chain protection (2-Cl-Z) is deblocked using DMS:HF:p-cresol (65:25:10, v/v) for 1 hour at 0° C. The polymer is dissolved in water, base treated with 1 N NaOH, dialyzed in 50 kD mol. wt. cut-off and lyophilized to obtain poly[0.57(GVGVP, 0.33(GFGVP), 0.1 (GKGVP)], as polymer IV.

EXPERIMENT 2

Attachment of Appropriate Redox Couples a. NAD attachment to polymer II.

Polymer II and HOBt in 2,2,2-trifluoroethanol (TFE) are cooled to −15° C. and EDCI is added. After stirring for 20 minutes a pre-cooled solution of NAD in water and NMM is added and stirred for 3 days at room temperature. After evaporating TFE, the residue is dissolved in water, dialyzed using 50 kD mol. wt. cut-off dialysis tubing and lyophilized to obtain poly[0.57(GVGVP)0.33(GFGVP)0.1 (GE{NAD}GVP)].

b. FAD attachment to polymer II

FAD is attached to the polymer II following the same synthetic procedure explained for the attachment of NAD.

Both NAD and FAD attached to polymer II are useful for testing the effects of added pressure on their reduction potential in a pressurized cell.

c. N-Me-nicotinic acid attachment to polymer IV

The carboxylic group of N-methyl nicotinic acid is activated by EDCI in the presence of HOBt and made to react with the epsilon-$NH_2$ group of lysine in polymer IV. After three days stirring, the unreacted reagents and byproducts are removed by 50 kD dialysis and the sample is lyophilized.

This polymer is useful for testing the effects of pressure on oxidation state.

EXPERIMENT 3

Construction of a Transparent Pressurizable Cell for Potentametric Studies a. The pressure cell design allows for pressurization to 100 atmospheres. A quartz tube is used with a 10 mm inner diameter and a 2 mm wall thickness which is fitted into stainless steel end plates with an O-ring seal. Concentric with this, a pyrex tube is fitted in the end plates with an O-ring seal making the cell thermostatable. The end plates would have a port in the center for access to the sample area. Fittings for the ports are configured to allow for applying and monitoring pressure and would contain electrodes for potentiometric measurement and control. Also the approach of Disteche, A., "pH Measurements with a Glass Electrode Withstanding 1500 kg/$cm_2$ Hydrostatic Pressure", *Rev. Sci. Instr.,* 30:474–478 (1959) for achieving pH measurements under high pressure can be integrated into the design.

EXPERIMENT 4

The Inverse Temperature Transition $T_t$ Coupled to the Oxidative State of Dinucleotide It has been demonstrated that the value of $T_t$ changes with the oxidative state of the nicotinamide adenine dinucleotide (NAD) and flavin adenine dinucleotide (FAD). Covalent attachment of the oxidized dinucleotide by amide linkage between the Glu residue carboxyl moiety and the adenine $NH_2$ moiety causes a small increase in the value of $T_t$ for the NAD addition and in the value of $T_t$ for the FAD addition when compared to the Glu(COOH) state of the polypentapeptide for phosphate buffered saline (0.15 N NaCl, 0.01 M phosphate). Significantly for both dinucleotides, on reduction of the nicotinamide moiety by dithionite caused a lowering of the $T_t$ by 40° C. and of the flavin moiety caused a lowering of the value of $T_t$. Thus, the above perturbations of $T_t$, for oxidation and reduction can be used to drive unfolding and folding, respectively, and with the use of the hydrophobicity scale for the amino acid residues, the transition temperature of the polypentapeptide can be placed as desired. It is now possible to add the NAD and FAD prosthetic functional groups to the hydrophobicity scale as shown in Table 1.

EXPERIMENT 5

Baroelectrical Transduction (Piezoelectric Effect)

It has been found that the attachment of flavin adenine dinucleotide (FAD) by amide linkage to a Glu carboxyl moiety results in a protein-based polymer that changes its transition temperature on reduction. Accordingly, both nicotinamide adenine dinucleotide (NAD) and FAD are attached to polymer II and the effect of added pressure on their reduction potential is examined in the pressurizable cell.

Also poly[0.57(GVGVP),0.33(GFGVP),0.1(GKGVP)] polymer IV, is synthesized in order to use carboxyl moieties appropriate for attachment by amide linkage to the epsilon-$NH_2$ of Lys(K). The entity attached is N-methyl nicotinate. This too is tested as the cross-linked elastomeric matrix for the effect of pressure on oxidative state.

Conclusion:

Using poly($Val^1$-Pro2-Gly3-Val4-Gly5), i.e., poly(VPGVG), as the parent molecular system which exhibits composition and solute dependent inverse temperature transitions of hydrophobic folding on raising the temperature, the dinucleotides—nicotinamide adenine dinucleotide (NAD) and flavine adenine dinucleotide (FAD)—were each attached by amide linkage between the $NH_2$ of the adenine ring and the γCOOH of the Glu(E) residue in poly[fv(VPGVG)fx(VPGEG)] where fv and fx are mole fractions with fv+fx=1. With the definitions of E'=Glu(NAD) and E"=Glu(FAD), the transition temperature, $T_t$, can be found for E' and E" analogs and extrapolated to fx=1. Significantly on reduction by sodium dithionite, the transition temperature is lowered for E' (reduced) and for E" (reduced) when extrapolated to fx=1 and corrected for the added salt concentration.

By lowering the temperature of the inverse temperature transition, reduction of the dinucleotide while at a temperature just below $T_t$ for the polypeptide or protein can be used to drive hydrophobic folding, that is, electromechanical transduction. Accordingly, oxidation/reduction joins protonation/deprotonation, phosphorylation/dephosphorylation, compression/decompression, changes in solute concentration, etc., in shifting the temperature of inverse temperature transitions as a means of achieving free energy transduction in polypeptides and proteins.

All publications and patent applications mentioned in this specification are herein incorporated by reference to the same extent as if each individual publication or patent application was specifically and individually indicated to be incorporated by reference at the location where cited.

The invention now being fully described, it will be apparent to one of ordinary skill in the art that many changes and modifications can be made thereto without departing from the spirit or scope of the appended claims.

What is claimed is:

1. A bioelastic polymer responsive to electrical energy, comprising:
   a bioelastomeric polypeptide having an inverse temperature transition and containing a repeating unit that contains a beta turn, wherein at least one amino acid residue in the bioelastomeric unit has a side chain that responds to a change in exposure to electrical energy in the absence of light to effect a change in polarity or hydrophobicity of the side chain and is present in sufficient amount to provide a shift in the temperature of inverse temperature transition of the polymer upon the change in exposure to electrical energy.

2. The bioelastic polymer of claim 1, wherein the reaction of the responsive side chain is reversible.

3. The bioelastic polymer of claim 1, wherein only a fraction of bioelastomeric repeating units in the polymer contain said side chain that responds to a change in exposure to electrical energy.

4. The bioelastic polymer of claim 1, wherein the temperature of inverse temperature transition is in the range of liquid water.

5. The bioelastic polymer of claim 1, wherein the bioelastomeric units are selected from the group consisting of bioelastic pentapeptides, tetrapeptides, and nonapeptides.

6. The bioelastic polymer of claim 1, which further comprises a second amino acid having a side chain capable of undergoing a change in an aqueous environment.

7. The bioelastic polymer of claim 6, wherein said second amino acid side chain undergoes a chemical change.

8. The bioelastic polymer of claim 1, wherein the change in hydrophobicity of the responsive side chain is equal to or greater than the hydrophobicity of a $CH_2$ group.

9. A composition that expands or contracts upon a change in exposure to electrical energy, which comprises:
   a polymeric material having an inverse temperature transition, wherein at least a fraction of the bioelastomeric repeating units in said polymer contain an electroresponsive side chain that responds to a change in exposure to electrical energy in the absence of light to effect a change in the polarity or hydrophobicity of the side chain and that is present in sufficient amount to provide a shift in the temperature of inverse temperature transition of the polymer upon the change in exposure to electrical energy.

10. The composition of claim 9, wherein the polymer comprises a series of β-turns separated by dynamic bridging segments suspended between said β-turns.

11. The composition of claim 10, wherein the polymer consists essentially of polypeptide bioelastomeric units, each of which comprises a β-turn.

12. The composition of claim 10, wherein the polymer comprises multiple polypeptide bioelastomeric repeating units, each of which comprises a β-turn, and further comprises intervening polypeptide segments between at least some bioelastomeric repeating units.

13. The composition of claim 9, wherein at least a fraction of said elastomeric units comprise a VPGVG repeating unit.

14. The composition of claim 13, wherein the polymer comprises a segment having the formula poly[$f_x$(VPGXG), $f_y$(VPGVG)] where $f_x$ and $f_y$ are mole fractions with $f_x+f_y=1$ and X represents said amino acid residue having an electrically responsive side chain.

15. The composition of claim 13, wherein said polymer comprises a segment having the formula poly[$f_x$(VPGXG), $f_y$(VPGVG), $f_z$(VPGZG)] where $f_x$, $f_y$, and $f_z$ are mole fractions with $f_x+f_y+f_z=1$, X represents the amino acid residue having a electrically responsive side chain, and Z represents an amino acid residue having a side chain capable of undergoing a chemical change in an aqueous environment.

16. A method of producing mechanical work, which comprises:

changing electrical energy exposure of a bioelastic polymer containing bioelastomeric units having an inverse temperature transition, wherein at least one amino acid residue in a bioelastomeric unit has a side chain that responds to a change in exposure to electrical energy in the absence of light to effect a change in the polarity or hydrophobicity of the electrically responsive side chain and that is present in sufficient amount to provide a shift in the temperature of inverse temperature transition of the polymer upon the change in exposure to electrical energy, and wherein said polymer is constrained so that expansion or contraction of said polymer produces mechanical work.

17. The method of claim 16, wherein when the electrical energy exposure is changed an object in contact with the polymer which is under the influence of a force resisted by the polymer moves under the influence of the force as the polymer contracts or expands.

18. An apparatus for producing mechanical work, which comprises:

a bioelastic polymer containing bioelastomeric units having an inverse temperature transition, wherein at least one amino acid residue in a bioelastomeric unit has a side chain that reacts to a change in exposure to electrical energy in the absence of light to effect a change in the polarity or hydrophobicity of the electrically responsive side chain and is present in sufficient amount to provide a shift in the temperature of inverse temperature transition of the polymer upon the change in exposure to electrical energy;

means for constraining said polymer wherein expansion of said polymer will produce mechanical work; and means for applying a change in exposure in electrical energy to the polymer, whereby a change in the electrical energy causes the polymer to expand and produce the mechanical work.

19. A method of producing a pH change in an environment, which comprises:

locating in said environment a bioelastic polymer containing bioelastomeric units having an inverse temperature transition, wherein (1) at least one amino acid residue in a bioelastomeric unit has a side chain that reacts to a change in exposure to electrical energy in the absence of light to effect a change in the polarity or hydrophobicity of the electrically responsive side chain and that is present in sufficient amount to provide a shift in the temperature of inverse temperature transition of the polymer upon the change in exposure to electrical energy, and (2) at least a fraction of said bioelastomeric units contain at least one amino acid residue with a side chain capable of undergoing reversible protonation, and applying a change in exposure to electrical energy to said environment, whereby the electrical energy change causes a change in the pKa of the polymer and a resulting change of pH in the environment.

20. An apparatus for producing changes in pH in an environment, which comprises:

a bioelastic polymer containing bioelastomeric units having an inverse temperature transition, wherein (1) at least one amino acid residue in a bioelastomeric unit has a side chain that reacts to a change in exposure to electrical energy in the absence of light to effect a change in the polarity or hydrophobicity of the side chain and that is present in sufficient amount to provide a shift in the temperature of inverse temperature transition of the polymer upon the change in exposure to electrical energy; and means for applying a change in exposure to electrical energy to said polymer, whereby the change in electrical energy causes said polymer to undergo a change in pKa and change the pH in the environment.

21. An electrically responsive bioelastic polymer machine of the first order $T_t$-type, comprising the electrically responsive polymer of claim 1.

22. An electrically responsive bioelastic polymer machine of the second order $T_t$-type, comprising the composition of claim 6.

23. An electrochemical device for desalinating sea water or brackish water by the conversion of electrical energy to chemical work, which comprises:

a) a housing containing a bioelastomeric material capable of stretching in response to a change in exposure to electrical energy in the absence of light thereby allowing salt-diminished water to move into the bioelastomeric material while substantially repelling solvated salt ions from entry thereto, b) means for application of a change in exposure of electrical energy to the bioelastic polymer in the housing, c) means for uptake of the sea water or brackish water into the housing, means for draining concentrated saltwater from said housing, and means for draining desalinated water from the housing, wherein the bioelastomeric material is capable of reversibly contracting and relaxing by means of an inverse temperature transition shift induced by electrical energy.

24. A polymer responsive to electrical energy, comprising:

a bioelastic polymer containing tetrapeptide or pentapeptide repeating units or mixtures thereof, wherein said repeating units comprise amino acid residues selected from the group consisting of hydrophobic amino acid and glycine residues and wherein said repeating units exist in a conformation having a β-turn, wherein said polymer comprises at least one amino acid residue having a side chain that reacts to a change in exposure to electrical energy to effect a change in the polarity or hydrophobicity of the electroresponsive side chain, said electroresponsive side chain being present in an amount sufficient to provide a shift in the temperature of a inverse temperature transition of said polymer upon said change in exposure of said polymer to electrical energy, wherein response of said electroresponsive side chain upon a change in exposure to electrical energy is an ionization, deionization, oxidation, reduction, amidation, deamidation, phosphorylation, dephosphorylation, isomerization, dimerization, hydrolysis or addition reaction.

25. The electroresponsive polymer of claim 24, wherein response of said electroresponsive side chain upon a change in exposure to electrical energy is an oxidation or reduction reaction.

* * * * *